United States Patent [19]

Wenger et al.

[11] Patent Number: 4,746,352
[45] Date of Patent: May 24, 1988

[54] 3-(5-CARBOXY-4-SUBSTITUTED-PHENYL)-(THIO)URACIL-ESTERS AND SALTS

[75] Inventors: Jean Wenger, Uster; Paul Winternitz, Greifensee, both of Switzerland

[73] Assignee: Hoffmann-La Roche Inc., Nutley, N.J.

[21] Appl. No.: 837,986

[22] Filed: Mar. 10, 1986

[30] Foreign Application Priority Data

Mar. 20, 1985 [CH] Switzerland ............ 1240/85
Feb. 6, 1986 [CH] Switzerland ............ 460/86

[51] Int. Cl.⁴ ............ A01N 43/54; A01N 43/10; C07D 239/95; C07D 239/96
[52] U.S. Cl. ............ 71/90; 71/92; 544/253; 544/278; 544/285; 544/311; 544/312; 544/313; 544/314
[58] Field of Search ............ 544/312, 311, 313, 278, 544/253, 285, 314; 71/90, 92

[56] References Cited

U.S. PATENT DOCUMENTS 3,330,640 7/1967 Luckenbaugh ............ 544/314
4,266,056 5/1981 Henrick et al. ............ 544/314
4,329,460 5/1982 Miyashita et al. ............ 544/314

FOREIGN PATENT DOCUMENTS 1924232 11/1969 Fed. Rep. of Germany .
2043629 12/1979 United Kingdom .

OTHER PUBLICATIONS

Eckstein et al., Chem. Abs., vol. 94 (1981).

Primary Examiner—Glennon H. Hollrah
Assistant Examiner—James H. Turnipseed
Attorney, Agent, or Firm—Jon S. Saxe; George M. Gould; Dennis P. Tramaloni

[57] ABSTRACT

The disclosure is concerned with novel 3-aryluracils of the formula

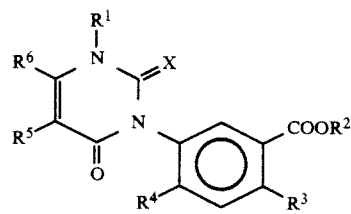

I wherein $R^1$, $R^2$, $R^3$, $R^4$, $R^5$, $R^6$ and X have the significances given in the description, as well as salts thereof and their manufacture, weed control compositions which contain such compounds as active ingredients and the use of the active ingredients or compositions for the control of weeds. The disclosure also concerns certain herbicidally active starting materials and weed control compositions containing these as active ingredients.

21 Claims, No Drawings

3-(5-CARBOXY-4-SUBSTITUTED-PHENYL)-(THIO)URACIL-ESTERS AND SALTS

SUMMARY OF THE INVENTION

The present invention is concerned with heterocyclic compounds, especially 3-aryluracils of the general formula

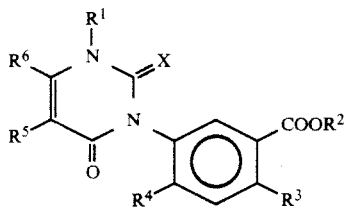

wherein $R^1$ is hydrogen, alkyl, alkenyl, alkynyl, alkoxyalkyl, formyl, alkanoyl or alkoxycarbonyl, $R^2$ is hydrogen, alkyl, alkenyl, alkynyl or alkoxyalkyl, $R^3$ is halogen or nitro, $R^4$ is hydrogen or halogen, $R^5$ is hydrogen, halogen, alkyl, chloromethyl, bromomethyl, hydroxymethyl, alkoxymethyl, alkylthiomethyl, cyano, nitro or thiocyanato, $R^6$ is hydrogen, alkyl or fluoroalkyl, or $R^5$ and $R^6$ together signify tri- or tetramethylene in which one methylene can be replaced by oxygen or sulphur and which is optionally substituted with alkyl, and X signifies oxygen or sulphur, with the provisos that (i) $R^6$ signifies exclusively alkyl or fluoroalkyl where $R^5$ is fluorine and (ii) $R^6$ signifies exclusively hydrogen or alkyl and X exclusively oxygen where $R^5$ is cyano, and salts of those compounds of formula I in which $R^1$ and-/or $R^2$ is hydrogen. Those compounds of formula I in which $R^1$ and $R^2$ are different from hydrogen (compounds of the general formula I' hereinafter) have herbicidal activity and are suitable as active substances of weel control compositions. Further aspects of the present invention are the manufacture of the compounds I and their salts, weed control compositions containing compounds of formula I' as the active substance, a method of controlling weeds by treating the locus to be protected against weeds and/or the weeds with such compositions and the use of the compounds of formula I' for controlling weeds. Certain starting materials for the manufacture of the compounds of formula I, namely the compounds of the general formula

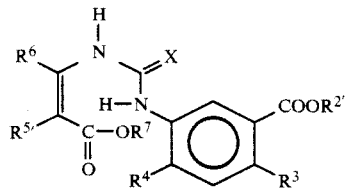

wherein $R^{2'}$ is alkyl, alkenyl, alkynyl or alkoxyalkyl, $R^3$, $R^4$ and $R^6$ are as given above, $R^{5'}$ is hydrogen, fluorine or alkyl or together with $R^6$ is optionally modified tri- or tetramethylene, as more precisely defined above, and $R^7$ is alkyl are new and constitute a still further aspect of the present invention. Some of these compounds of formula II, like the compound of formula I', have herbicidal activity.

DETAILED DESCRIPTION OF THE INVENTION

The present invention is concerned with heterocyclic compounds, namely 3-aryluracils of the general formula

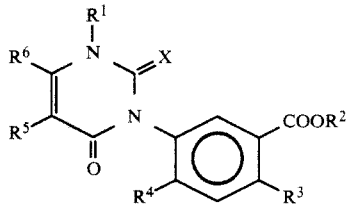

wherein
- $R^1$ signifies hydrogen, $C_{1-4}$-alkyl, $C_{2-4}$-alkenyl, $C_{2-4}$-alkynyl, $C_{2-6}$-alkoxyalkyl, formyl, $C_{2-6}$-alkanoyl or $C_{2-6}$-alkoxycarbonyl,
- $R^2$ signifies hydrogen, $C_{1-6}$-alkyl, $C_{2-4}$-alkenyl, $C_{2-4}$-alkynyl or $C_{2-6}$-alkoxyalkyl,
- $R^3$ signifies halogen or nitro,
- $R^4$ signifies hydrogen or halogen,
- $R^5$ signifies hydrogen, halogen, $C_{1-4}$-alkyl, chloromethyl, bromomethyl, hydroxymethyl, ($C_{1-5}$-alkoxy)methyl, ($C_{1-5}$-alkylthio)methyl, cyano, nitro or thiocyanato,
- $R^6$ signifies hydrogen, $C_{1-4}$-alkyl or $C_{1-4}$-fluoroalkyl, or
- $R^5$ and $R^6$ together signify tri- or tetramethylene in which one methylene can be replaced by oxygen or sulphur and which is optionally substituted with $C_{1-3}$-alkyl, and
- X signifies oxygen or sulphur, with the proviso that (i) $R^6$ signifies exclusively $C_{1-4}$-alkyl or $C_{1-4}$-fluoroalkyl where $R^5$ stands for fluorine and (ii) $R^6$ signifies exclusively hydrogen or $C_{1-4}$-alkyl and X signifies exclusively oxygen where $R^5$ stands for cyano, as well as salts of those compounds of formula I in which $R^1$ and/or $R^2$ signifies hydrogen.

Those compounds of formula I in which $R^1$ and $R^2$ are different from hydrogen, i.e. the compounds of the general formula

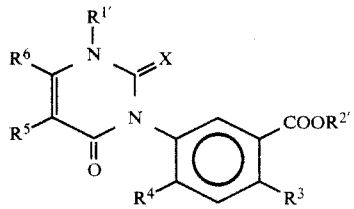

wherein
- $R^{1'}$ signifies $C_{1-4}$-alkyl, $C_{2-4}$-alkenyl, $C_{2-4}$-alkynyl, $C_{2-6}$-alkoxyalkyl, formyl, $C_{2-6}$-alkanoyl or $C_{2-6}$-alkoxycarbonyl,
- $R^{2'}$ signifies $C_{1-4}$-alkyl, $C_{2-4}$-alkenyl, $C_{2-4}$-alkynyl or $C_{2-6}$-alkoxyalkyl and
- $R^3$, $R^4$, $R^5$, $R^6$ and X have the significances given above, with the above-indicated provisos (i) and (ii), have herbicidal activity and are suitable as active substances of weed control compositions. The remaining compounds of formula I, i.e. those in which $R^1$ and/or $R^2$ signify hydrogen as well as the salts of these compounds, are primarily suitable as starting materials for the manufacture of the compounds of formula I'; however some of these remaining compounds I also have herbicidal properties.

The invention also embraces weed control compositions which contain compounds of formula I' as the active substance, processes for the manufacture of the compounds in accordance with the invention as well as the use of the compounds of formula I' or compositions for the control of weeds.

In formula I or I' above "halogen" embraces fluorine chlorine, bromine and iodine. The alkyl, alkenyl and alkynyl residues can be straight-chain or branched, whereby this also applies to the or each alkyl part of the alkoxyalkyl, alkanoyl, alkoxycarbonyl, alkoxymethyl, alkylthiomethyl and fluoroalkyl groups. The fused rings formed by $R^5$ and $R^6$ are exemplified by the following partial structures:

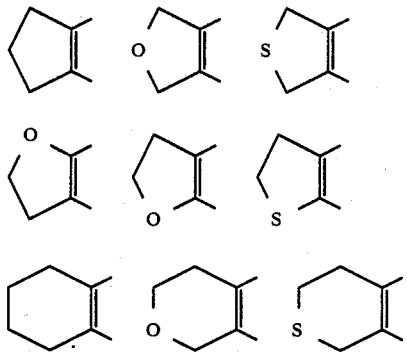

A $C_{1-4}$-fluoroalkyl group can have one or more fluorine atoms, whereby trifluoromethyl may be named as an example of a multiply fluorinated alkyl group.

The salts of the compounds of formula I are especially alkali metal salts, e.g. sodium and potassium salts; alkaline earth metal salts, e.g. calcium and magnesium salts; ammonium salts, i.e. unsubstituted ammonium salts and mono- or multiply-substituted ammonium salts, e.g. triethylammonium and methylammonium salts, as well as salts with other organic bases, e.g. with pyridine.

The possible presence of at least one asymmetric carbon atom in the compounds of formula I or I' means that the compounds can occur in optically isomeric forms. Geometric isomerism can also occur when an aliphatic C═C double bond is present. Moreover, in those compounds of formula I in which $R^1$ signifies hydrogen the occurrence of keto-enol tautomerism (—NH—CX—⇌—N═C(XH)—) cannot be excluded. Formula I or I' is intended to embrace all of these possible isomeric forms as well as mixtures thereof.

When $R^1$ or $R^{1'}$ or $R^2$ or $R^{2'}$ signifies $C_{2-4}$-alkenyl or $C_{2-4}$-alkynyl, this residue is preferably allyl or propargyl, respectively. As the $C_{2-6}$-alkanoyl group there preferably comes into consideration $C_{2-4}$-alkanoyl, while the $C_{2-4}$-alkoxycarbonyl groups are the preferred $C_{2-6}$-alkoxycarbonyl groups. In general, a halogen atom which may be present is preferably fluorine, chlorine or bromine.

Independently of each other $R^1$ or $R^{1'}$ preferably signifies straight-chain $C_{1-4}$-alkyl (especially methyl); $R^2$ or $R^{2'}$ preferably signifies $C_{1-6}$-alkyl or $C_{2-6}$-alkoxyalkyl; $R^3$ preferably signifies chlorine or bromine; $R^4$ preferably signifies fluorine; $R^5$ preferably signifies hydrogen, fluorine, chlorine, bromine or straight-chain $C_{1-4}$-alkyl (especially methyl or ethyl); and $R^6$ preferably signifies straight-chain $C_{1-4}$-alkyl (especially methyl or ethyl) or $C_{1-4}$-fluoroalkyl (especially trifluoromethyl). It is also preferred that $R^5$ and $R^6$ together signify tri- or tetramethylene. X is preferably oxygen.

Especially preferred compounds of formula I or I' are:

Isopropyl 2-chloro-4-fluoro-5-(1,2,4,5,6,7-hexahydro-1-methyl-2,4-dioxo-3H-cyclopenta[d]pyrimidin-3-yl)-benzoate, isopropyl 2-chloro-4-fluoro-5-[1,4,5,6,7-hexahydro-1-methyl-2,4-dioxo-3(2H)-quinazolinyl]-benzoate, isopropyl 2-chloro-4-fluoro-5-[3,6-dihydro-3,4-dimethyl-2,6-dioxo-1(2H)-pyrimidinyl]-benzoate, isopropyl 2-chloro-4-fluoro-5-[5-bromo-3,6-dihydro-3,4-dimethyl-2,6-dioxo-1(2H)-pyrimidinyl]-benzoate, isopropyl 2-chloro-4-fluoro-5-[3,6-dihydro-3,4-dimethyl-5-fluoro-2,6-dioxo-1(2H)-pyrimidinyl]-benzoate, isopropyl 2-chloro-4-fluoro-5-[3,6-dihydro-3,4-dimethyl-5-iodo-2,6-dioxo-1(2H)-pyrimidinyl]-benzoate, isopropyl 2-chloro-4-fluoro-5-[3,6-dihydro-3,4-dimethyl-5-hydroxymethyl-2,6-dioxo-1(2H)-pyrimidinyl]-benzoate, isopropyl 2-chloro-4-fluoro-5-[3,6-dihydro-4-ethyl-3-methyl-2,6-dioxo-1(2H)-pyrimidinyl]-benzoate, isopropyl 2-chloro-4-fluoro-5-[3,6-dihydro-3-methyl-4-propyl-2,6-dioxo-1(2H)-pyrimidinyl]-benzoate, isopropyl 2-chloro-4-fluoro-5-[3,6-dihydro-3-methyl-4-trifluoromethyl-2,6-dioxo-1(2H)-pyrimidinyl]-benzoate, isopropyl 2-bromo-4-fluoro-5-(1,2,4,5,6,7-hexahydro-1-methyl-2,4-dioxo-3H-cyclopenta[d]pyrimidin-3-yl)-benzoate, isopropyl 2-chloro-4-fluoro-5-[3,6-dihydro-5-fluoro-3-methyl-4-trifluoromethyl-2,6-dioxo-1(2H)-pyrimidinyl]-benzoate, isopropyl 2-chloro-4-fluoro-5-[3,6-dihydro-3,4-dimethyl-5-nitro-2,6-dioxo-1(2H)-pyrimidinyl]-benzoate, 2-methoxy-1-methylethyl 2-chloro-4-fluoro-5-(1,2,4,5,6,7-hexahydro-1-methyl-2,4-dioxo-3H-cyclopenta[d]pyrimidin-3-yl)-benzoate and tert.butyl 2-chloro-4-fluoro-5-(1,2,4,5,6,7-hexahydro-1-methyl-2,4-dioxo-3H-cyclopenta[d]pyrimidin-3-yl)-benzoate.

Other representatives of the compounds of formula I or I' are:

2-Methoxyethyl 2-chloro-4-fluoro-5-(1,2,4,5,6,7-hexahydro-1-methyl-2,4-dioxo-3H-cyclopenta[d]pyrimidin-3-yl)-benzoate, ethyl 2-chloro-4-fluoro-5-(1,2,4,5,6,7-hexahydro-1-methyl-2,4-dioxo-3H-cyclopenta[d]pyrimidin-3-yl)-benzoate and propyl 2-chloro-4-fluoro-5-(1,2,4,5,6,7-hexahydro-1-methyl-2,4-dioxo-3H-cyclopenta[d]pyrimidin-3-yl)-benzoate.

The process in accordance with the invention for the manufacture of the compounds of formula I and their salts is characterized by (a) for the manufacture of those compounds of formula I in which $R^1$ signifies hydrogen and $R^2$ signifies $C_{1-6}$-alkyl, $C_{2-4}$-alkenyl, $C_{2-4}$-alkynyl or $C_{2-6}$-alkoxyalkyl and $R^5$ has a significance other than chlorine, bromine, iodine, chloromethyl, bromomethyl, hydroxymethyl, ($C_{1-5}$-alkoxy)methyl, ($C_{1-5}$-alkylthio)methyl, cyano, nitro or thiocyanato, as well as of metal salts of those compounds of fomula I in which $R^1$ signifies hydrogen, subjecting a compound of the general formula

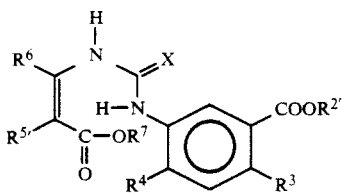

wherein $R^{2'}$ signifies $C_{1-6}$-alkyl, $C_{2-4}$-alkenyl, $C_{2-4}$-alkynyl or $C_{2-6}$-alkoxyalkyl, $R^3$, $R^4$, $R^6$ and X have the significances given above, $R^{5'}$ signifies hydrogen, fluorine, $C_{1-4}$-alkyl or together with $R^6$ tri- or tetramethylene which is optionally modified as more precisely defined above, and $R^7$ signifies lower alkyl, preferably $C_{1-4}$-alkyl, to a base-catalyzed cyclization and, if desired, converting a metal salt form of the uracil derivative which may be obtained into the corresponding acid form ($R^1$=hydrogen) by treatment with an acid, (b) for the manufacture of those compounds of formula I in which $R^1$ signifies $C_{1-4}$-alkyl, $C_{2-4}$-alkenyl, $C_{2-4}$-alkynyl, $C_{2-6}$-alkoxyalkyl, formyl, $C_{2-6}$-alkanoyl or $C_{2-6}$-alkoxycarbonyl, subjecting a uracil derivative of the general formula

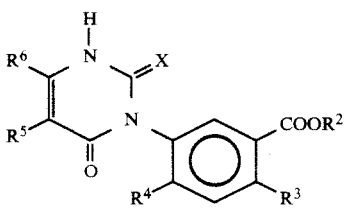

wherein $R^2$, $R^3$, $R^4$, $R^5$, $R^6$ and X have the significances given above, to an alkylation or acylation with a corresponding alkylating or acylating agent containing a $C_{1-4}$-alkyl, $C_{2-4}$-alkenyl, $C_{2-4}$-alkynyl, $C_{2-6}$-alkoxyalkyl, formyl, $C_{2-6}$-alkanoyl or $C_{2-6}$-alkoxycarbonyl group, (c) for the manufacture of those compounds of formula I in which $R^1$ signifies $C_{1-4}$-alkyl, $C_{2-4}$-alkenyl, $C_{2-4}$-alkynyl or $C_{2-6}$-alkoxyalkyl, $R^5$ is different from chlorine, bromine, iodine, chloromethyl, bromomethyl, hydroxymethyl, ($C_{1-5}$-alkoxy)methyl, ($C_{1-5}$-alkylthio)methyl, cyano, nitro or thiocyanato and X signifies sulphur, reacting a compound of the general formula

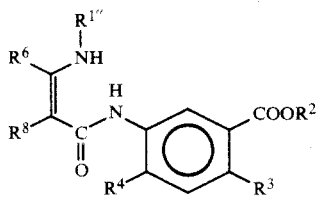

wherein $R^{1''}$ signifies $C_{1-4}$-alkyl, $C_{2-4}$-alkenyl, $C_{2-4}$-alkynyl or $C_{2-6}$-alkoxyalkyl, $R^2$, $R^3$, $R^4$ and $R^6$ have the significances given above, and $R^8$ signifies fluorine, $C_{1-4}$-alkyl, ($C_{1-4}$-alkoxy)carbonyl or together with $R^6$ tri- or tetramethylene which is optionally modified as more precisely defined above, whereby in the case that $R^8$ signifies fluorine, $R^6$ is $C_{1-4}$-alkyl or $C_{1-4}$-fluoroalkyl, with N,N'-thiocarbonyldiimidazolide or thiophosgene and, if $R^8$ signifies ($C_{1-4}$-alkoxy)carbonyl, submitting the so produced 5-alkoxycarbonyl-2-thiouracil of the general formula

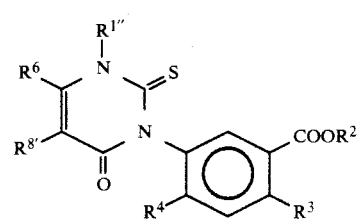

wherein $R^{1''}$, $R^2$, $R^3$, $R^4$ and $R^6$ have the significances given above and $R^{8'}$ signifies ($C_{1-4}$-alkoxy)carbonyl, to a hydrolysis and a decarboxylation, (d) for the manufacture of those compounds of formula I in which $R^5$ signifies chlorine, bromine or iodine, chlorinating, brominating or iodinating a uracil derivative of the general formula

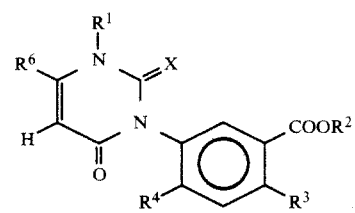

wherein $R^1$, $R^2$, $R^3$, $R^4$, $R^6$ and X have the significances given above, (e) for the manufacture of those compounds of formula I in which $R^5$ signifies chloro- or bromomethyl, (i) treating a uracil derivative of formula Ib above with chloro- or bromomethoxymethane or (ii) treating a 5-hydroxymethyluracil of the general formula

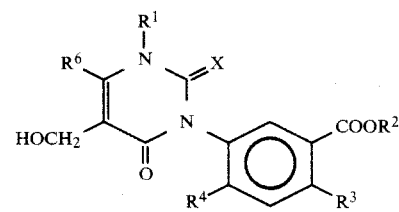

wherein $R^1$, $R^2$, $R^3$, $R^4$, $R^6$ and X have the significances given above, with thionyl chloride or bromide or (iii) treating a 5-methyluracil of the general formula

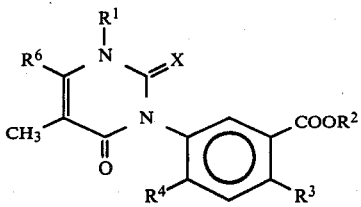

wherein $R^1$, $R^2$, $R^3$, $R^4$, $R^6$ and X have the significances given above, with N-chlorosuccinimide or N-bromosuccinimide, (f) for the manufacture of those compounds of formula I in which $R^5$ signifies hydroxymethyl, hydrolysing a 5-halomethyluracil of the general formula

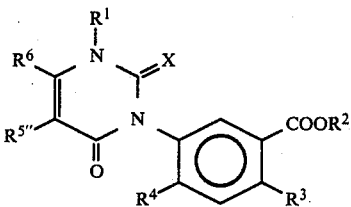

wherein $R^1$, $R^2$, $R^3$, $R^4$, $R^6$ and X have the significances given above and $R^{5''}$ signifies chloro-, bromo- or iodomethyl, (g) for the manufacture of those compounds of formula I in which $R^5$ signifies ($C_{1-5}$-alkoxy)methyl or ($C_{1-5}$-alkylthio)methyl, treating a 5-halomethyluracil of formula Ie given above, in which $R^{5''}$ signifies chloro- or bromomethyl, with an alkali metal alcoholate or thioalcoholate of the general formula $$R^9M \qquad\qquad V$$

wherein $R^9$ signifies $C_{1-5}$-alkoxy or $C_{1-5}$-alkylthio and M signifies an alkali metal, preferably sodium or potassium, or with a $C_{1-5}$-alkanol or $C_{1-5}$-alkylmercaptan, (h) for the manufacture of those compounds of formula I in which $R^5$ signifies ($C_{1-5}$-alkylthio)methyl, treating a 5-hydroxymethyluracil of formula Ic given above with a $C_{1-5}$-alkylmercaptan, (i) for the manufacture of those compounds of formula I in which $R^1$ signifies hydrogen, $R^5$ signifies cyano, $R^6$ signifies hydrogen or $C_{1-4}$-alkyl and X signifies oxygen, subjecting a compound of the general formula

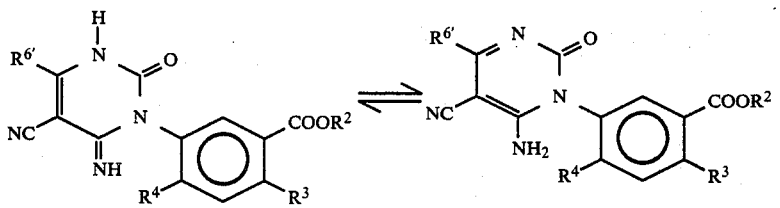

wherein $R^2$, $R^3$ and $R^4$ have the significances given above and $R^{6'}$ signifies hydrogen or $C_{1-4}$-alkyl, to an acid-catalyzed hydrolysis, (j) for the manufacture of those compounds of formula I in which $R^5$ signifies nitro, nitrating a uracil derivative of formula Ib given above, (k) for the manufacture of those compounds of formula I in which $R^5$ signifies thiocyanato, treating a uracil derivative of formula Ib given above with thiocyanogen, (l) for the manufacture of those compounds of formula I in which $R^2$ signifies hydrogen, hydrolyzing a benzoic acid ester of the general formula

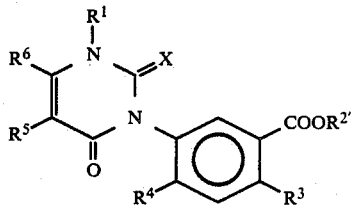

wherein $R^1$, $R^{2'}$, $R^3$, $R^4$, $R^5$, $R^6$ and X have the significances given above, to the corresponding benzoic acid, (m) for the manufacture of those compounds of formula I in which $R^2$ signifies $C_{1-6}$-alkyl, $C_{2-4}$-alkenyl, $C_{2-4}$-alkynyl or $C_{2-6}$-alkoxyalkyl, appropriately esterifying a benzoic acid of the general formula

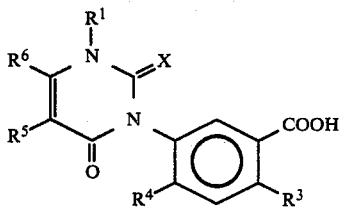

wherein $R^1$, $R^3$, $R^4$, $R^5$, $R^6$ and X have the significances given above, or a reactive derivative thereof, or (n) for the manufacture of those compounds of formula I in which $R^2$ signifies $C_{2-6}$-alkyl, $C_{2-4}$-alkenyl, $C_{2-4}$-alkynyl or $C_{2-6}$-alkoxyalkyl, subjecting a benzoic acid ester of formula If given above to a trans-esterification reaction with an alkanol, alkenol or alkynol of the general formula $$R^{2''}OH \qquad\qquad VII$$

wherein $R^{2''}$ signifies $C_{2-6}$-alkyl, $C_{2-4}$-alkenyl, $C_{2-4}$-alkynyl or $C_{2-6}$-alkoxyalkyl, whereby the reagent of formula VII is higher boiling that the alkanol, alkenol or alkynol $R^{2'}OH$, and, if desired, converting a thus-obtained compound of formula I in which $R^1$ and/or $R^2$ signifies hydrogen into a salt.

The cyclization according to process variant (a) can be carried out conveniently by treating the compound of formula II in an inert protic organic solvent such as an alcohol, e.g. methanol, ethanol or isopropanol; an inert aprotic organic solvent such as an aliphatic or cyclic ether, e.g. 1,2-dimethoxyethane, tetrahydrofuran or dioxan, or an aromatic, e.g. benzene or toluene; an inert aprotic, polar organic solvent, e.g. dimethylformamide or dimethyl sulphoxide, such solvents optionally being used in a two phase mixture with a hydrocarbon, e.g. n-hexane; or water with a base at temperatures between room temperature and the reflux temperature of the reaction mixture. As bases there come into consideration preferably sodium alcoholates, alkali metal hydroxides, especially sodium hydroxide and potassium hydroxide, alkali metal carbonates, especially sodium carbonate and potassium carbonate, and sodium hydride. Where an alkanol, alkenol or alkynol is used as the solvent, then this solvent conveniently corresponds to the pertinent hydroxy compound $R^{2'}OH$; thereby undesired competing trans-esterification reactions are avoided. When sodium hydride is used as the base, the solvent is preferably an aliphatic or cyclic ether, dimethylformamide or dimethyl sulphoxide.

After completion of the cyclization the product, when one of the above-mentioned bases or the like is used, is present in the form of the corresponding alkali metal salt. This can be isolated and purified in a manner known per se, or the mixture can be acidified in order to isolate the respective compound of formula I itself. A mineral acid such as hydrochloric acid or a strong organic acid such as acetic acid or p-toluenesulphonic acid is preferably used for this purpose.

In process variant (b) the term "alkylation" means the introduction of a $C_{1-4}$-alkyl, $C_{2-4}$-alkenyl, $C_{2-4}$-alkynyl or $C_{2-6}$-alkoxyalkyl group on the unsubstituted nitrogen atom of the uracil nucleus. Moreover, the term "acylation" applies analogously to the corresponding introduction of a formyl, $C_{2-6}$-alkanoyl or $C_{2-6}$-alkoxycarbonyl group. A $C_{1-4}$-alkyl, $C_{2-4}$-alkenyl, $C_{2-4}$-alkynyl or $C_{2-6}$-alkoxyalkyl halide, especially the respective chloride or bromide, or sulphate is conveniently used as the alkylating agent. As the acylating agent there comes into consideration especially a formic acid halide, a $C_{2-6}$-alkanoic acid halide or anhydride or $C_{1-5}$-alkyl chloro- or bromoformate, whereby the respective chloride or bromide is the preferred halide.

The alkylation is conveniently carried out in the presence of an inert, protic organic solvent such as a lower alkanol, e.g. ethanol, optionally in mixture with water; an inert, aprotic organic solvent such as an aliphatic or cyclic ether, e.g. 1,2-dimethoxyethane, tetrahydrofuran or dioxane; or an inert, aprotic, polar organic solvent, e.g. dimethylformamide or dimethyl sulphoxide, as well as in the presence of a base such as sodium hydride, an alkali metal alcoholate, especially sodium alcoholate, or an alkali metal carbonate, especially sodium carbonate, at temperatures between 0° C. and about 50° C., preferably at room temperature. In a preferred embodiment the uracil derivative of formula Ia is firstly treated with the base such as sodium hydride, ethanolate or carbonate in the solvent and after a short reaction time is treated with the halide in the case solvent. As a rule the reaction is completed, depending on the solvent used, within a relatively short time or after a few hours. The acylation with a halide can be carried out in a similar manner, although in this case it is carried out especially in an aprotic solvent and in the presence of sodium hydride as the base. When an alkanoic acid anhydride is used as the acylating agent, the acylation is suitably carried out without a base.

In the case of the alkylation of a uracil derivative of formula Ia in which X signifies sulphur mixtures of the pertinent N- and S-alkylated products are normally produced. The desired N-alkyl-, N-alkenyl, N-alkynyl- or N-alkoxyalkyluracil can be isolated from such a mixture by conventional methods; however it is advisable to employ process variant (c) in these cases.

The reaction according to process variant (c) is conventionally effected using N,N'-thiocarbonyldiimidazolide in the melt or thiophosgene in the presence of an aprotic organic solvent such as a chlorinated aliphatic hydrocarbon, e.g. 1,2-dichloroethane, or an aromatic, e.g. toluene, as well as in the presence of an organic tertiary base, such as triethylamine or pyridine. The reaction temperatures are generally in the range of about room temperature to 50° C., room temperature being preferred.

If a starting material of formula III is used in which $R^8$ signifies ($C_{1-4}$-alkoxy)carbonyl the so produced 5-alkoxycarbonyl-2-thiouracil of formula IV is then hydrolysed and decarboxylated to obtain the compound of formula I in which $R^5$ signifies hydrogen. This is conveniently effected in a single stage by briefly warming the product IV in the presence of aqueous hydrochloric acid or trifluoroacetic acid. In this case $R^{8'}$ preferably signifies tert.butoxycarbonyl.

The chlorination or bromination according to process variant (d) is conveniently carried out by means of elementary chlorine or sulphuryl chloride or elementary bromine or sulphuryl bromide, respectively, in the presence of an inert organic solvent such as acetic acid or a chlorinated aliphatic hydrocarbon, e.g. methylene chloride, chloroform or carbon tetrachloride, and in a temperature range of 0° C. to 60° C., preferably at room temperature. Moreover, the reaction can be carried out with the aid of an acid-binding agent, for which purpose sodium acetate and tertiary amines such as triethylamine, dimethylaniline and pyridine are especially preferred acid-binding agents.

The iodination according to this process variant is coveniently carried out using elementary iodine as the iodinating agent and a low-boiling aliphatic carboxylic acid such as acetic acid as the solvent and at temperatures between about 0° C. and about 110° C., preferably at room temperature. Moreover, it has been shown to be convenient to carry out the reaction in the presence of an acid such as fuming nitric acid. Saturated aqueous sodium bisulphite solution can be added after the completion of the reaction in order to remove excess iodine.

Process variant (e) (i) involves the direct introduction of a chloromethyl or bromomethyl group in the unsubstituted 5-position of the uracil nucleus, whereby the uracil derivative of formula Ib is reacted with chloro- or bromomethoxymethane, conveniently in the absence of a diluent and at elevated temperature, preferably in the temperature range of about 80° C. to about 140° C., especially at about 100° C. The reaction can be carried out, for example, in a heated closed reaction vessel under its own pressure.

Process variant (e) (ii) can alos be carried out without a diluent. Where a diluent is used, this is conveniently a chlorinated aliphatic hydrocarbon such as methylene chloride, chloroform or carbon tetrachloride. Moreover, the reaction is conveniently carried out at temperatures between 0° C. and 40° C., preferably at room temperature.

Process variant (e) (iii) comes into consideration as a further process for the manufacture of the 5-chloromethyl- and 5-bromomethyluracils in accordance with the invention. This is conveniently carried out by treating the 5-methyluracil of formula Id with N-chloro- or N-bromosuccinimide in the presence of a diluent, preferably a chlorinated hydrocarbon, such as carbon tetrachloride, at elevated temperature, preferably at temperatures between 70° C. and 100° C. It has been shown to be advantageous to carry out the reaction with the aid of a radical-forming catalyst such as dibenzoyl peroxide and/or under UV-irradiation.

The reaction according to process variant (f) can be carried out conveniently by reacting the 5-halomethyluracil of formula Ie with an aqueous solution of an inorganic base such as an alkali metal carbonate or bicarbonate, especially sodium carbonate or bicarbonate, at temperatures between 0° C. and 70° C., preferably at room temperature.

In process variant (g) the alkali metal alcoholate or thioalcoholate is conveniently produced in situ, in particular by reacting the alkali metal with the alcohol or mercaptan $R^9H$. The treatment of the 5-chloromethyl- or 5-bromomethyluracil of formula Ie with the alcoholate or thioalcoholate is then carried out in excess alcohol or mercaptan $R^9H$ as the diluent. If desired, the alcoholate or thioalcoholate can, however, firstly be isolated and, if desired, purified. In each case an auxiliary solvent such as an aliphatic or cyclic ether, especially 1,2-dimethoxyethane, tetrahydrofuran or dioxan, can be used. In the case of the treatment with the $C_{1-5}$-alkanol or $C_{1-5}$-alkylmercaptan $R^9H$ the reaction with an alkali metal is superfluous. In both cases the reaction is conveniently carried out at temperatures between 0° C. and the boiling point of the reaction mixture, preferably between room temperature and 70° C.

As an alternative, the 5-[($C_{1-5}$-alkylthio)methyl]-uracils can be manufactured according to process variant (h), whereby conveniently the corresponding 5-hydroxymethyluracil of formula Ic is treated with the $C_{1-5}$-alkylmercaptan in the presence of a solvent and at elevated temperature. The preferred solvents are lower alkanols, and the preferred reaction temperatures are from 100° C. to 150° C. The choice of the alcoholic solvent can depend on the nature of the pertinent group $R^2$ in the 5-hydroxymethyluracil Ic: if the 5-hydroxymethyluracil of formula Ic is a benzoic acid ester ($R^2$ signifies $C_{1-6}$-alkyl, $C_{2-4}$-alkenyl, $C_{2-4}$-alkynyl or $C_{2-6}$-alkoxyalkyl) and an alcohol, alkenol or alkynyl is used as the solvent, said solvent conveniently corresponds to the hydroxy compound $R^2OH$ used; in this way undesirable competing trans-esterifications are avoided.

The hydrolysis according to process variant (i) is conveniently carried out by means of a mineral acid such as hydrochloric acid in aqueous solution at temperatures between 20° C. and 100° C., preferably at room temperature. Water-miscible solvents such as lower alcohols and aliphatic or cyclic ethers, e.g. 1,2-dimethoxyethane, tetrahydrofuran and dioxan, can also be used, whereby the choice of an alcoholic solvent which may be used can depend, for the reason already given above, on the nature of the pertinent group $R^2$ in the compound VI.

The nitration according to process variant (j) is conveniently carried out by means of nitric acid or mixtures or solutions containing nitric acid such as especially mixtures of nitric acid, sulphuric acid and optionally also sulphur trioxide, solutions of nitric acid in glacial acetic acid and solutions of concentrated nitric acid in chlorinated hydrocarbons, e.g. methylene chloride, 1,2-dichloroethane and carbon tetrachloride. As a rule, the compound of formula Ib is introduced portion-wise into the nitrating medium and the mixture is stirred at room temperature or a slightly elevated temperature, i.e. up to about 50° C.

The thiocyanogen which is required in process variant (k) is conveniently produced in situ, for example by reacting lead or ammonium thiocyanate with bromine in the presence of a diluent at relatively low temperatures such as 0° C. to 30° C., preferably 0° C. to 10° C. Suitable diluents are halogenated aliphatic hydrocarbons such as methylene chloride and carbon tetrachloride and aliphatic or cyclic ethers such as 1,2-dimethoxyethane, tetrahydrofuran and dioxan, and in the case of ammonium thiocyanate also lower alkanoic acids such as acetic acid. The uracil derivative of formula Ib can be present from the outset in the reaction medium producing thiocyanogen, or it can be introduced subsequently into this medium, if desired after removing, e.g. by filtering, the still remaining solid constituents of the medium. In each case the temperature of the reaction mixture is conveniently held relatively low, in particular within the temperature range given above, until the reaction is completed.

The hydrolysis of the benzoic acid ester If according to process variant (l) can be carried out according to methods known per se, especially using an organic solvent in aqueous solution, such as aqueous alkanol, e.g. ethanol, or an aliphatic or cyclic ether, e.g. 1,2-dimethoxyethane, tetrahydrofuran or dioxan, in aqueous solution, and an inorganic base, such as sodium or potassium hydroxide, at temperatures between 0° C. and 70° C., preferably at room temperature.

Process variant (m) is an esterification of a substituted benzoic acid or a reactive derivative thereof, which can likewise be carried out according to methods known per se. Thus, for example, a salt of an acid of formula Ig is reacted with a $C_{1-6}$-alkyl, $C_{2-4}$-alkenyl, $C_{2-4}$-alkynyl or $C_{2-6}$-alkoxyalkyl chloride, bromide, iodide, sulphate, mesylate or tosylate in an inert diluent at temperatures from about room temperature to 100° C., e.g. at the reflux temperature of the reaction mixture, preferably in the temperature range of 40° C. to 70° C. As salts of the benzoic acid of formula Ig there come into consideration especially alkali metal salts, e.g. the sodium, potassium or lithium salt, alkaline earth metal salts, e.g. the magnesium, calcium or barium salt, and salts with organic bases such as tertiary amines, e.g. triethylamine, 1,5-diaza-bicyclo[4,3,0]non-5-ene, 1,8-diaza-bicyclo[5,4,0]undec-7-ene and 1,4-diaza-bicyclo[2,2,2]octane, whereby the alkali metal salts, especially the sodium salt, are preferred. The diluents which can be used are preferably inert organic solvents such as lower alkanols, e.g. ethanol, aliphatic and cyclic ethers, e.g. diethyl ether, tetrahydrofuran and dioxan, ketones, e.g. acetone and 2-butanone, dimethylformamide, dimethyl sulphoxide and hexamethylphosphoric acid triamide. The salt can be produced in situ by converting the acid with a suitable inorganic base, e.g. an alkali metal or alkaline earth metal carbonate or bicarbonate, or organic base into the salt, and this can subsequently be reacted with the second reactant in the same reaction mixture.

Where an acid halide of the benzoic acid of formula Ig is used as the reactive derivative, this is conveniently reacted with a $C_{1-6}$-alkanol, $C_{2-4}$-alkenol, $C_{2-4}$-alkynol or $C_{2-6}$-alkoxyalkanol in an inert organic solvent such as an aliphatic or cyclic ether, e.g. diethyl ether, tetrahydrofuran or dioxan, an aliphatic or aromatic hydrocarbon, e.g. n-hexane, benzene or toluene, or a halogenated, especially chlorinated, hydrocarbon, e.g. methylene chloride, chloroform or carbon tetrachloride, at temperatures of about −20° C. to 100° C., preferably from 0° C. to 50° C. Moreover, the reaction is conveniently carried out in the presence of an acid-binding agent such as an organic base, e.g. triethylamine, pyridine, 1,5-diaza-bicyclo[4,3,0]non-5-ene, 1,8-diaza-bicyclo[5,4,0]undec-7-ene or 1,4-diaza-bicyclo[2,2,2]octane. The acid halide is preferably the acid chloride.

As further possible reactive derivatives of the benzoic acid of formula Ig there can be mentioned the corresponding O-acyl-1,3-dicyclohexylisourea and the corresponding N-acylimidazole or acid anhydride. Such derivatives can be reacted with a $C_{1-6}$-alkanol, $C_{2-4}$-alkenol, $C_{2-4}$-alkynol or $C_{2-6}$-alkoxyalkanol in the same manner as the acid halide in order to obtain the desired benzoic acid esters. In these cases, however, the use of an acid-binding agent is superfluous.

The reaction according to process variant (n) can be carried out conveniently by heating the benzoic acid ester of formula If in excess alkanol, alkenol or alkynol of formula VII in the presence of a basic catalyst such as sodium cyanide, preferably at the reflux temperature of the reaction mixture. In the course of the reaction the residue $R^{2'}$ of the benzoic acid ester of formula If is replaced by the residue $R^{2''}$ from the compound of formula VII, whereby the alkanol, alkenol or alkynol of the formula $R^{2'}OH$, which boils lower than the compound VII, is liberated.

The salts of the thus-obtained compounds of formula I in which $R^1$ and/or $R^2$ signifies hydrogen can be manufactured in a manner known per se such as, for example, by dissolving the compound of formula I in a solution of the appropriate inorganic or organic base. As a rule, the salt formation is carried out within a short time at room temperature. In one embodiment the sodium salt is manufactured by dissolving the uracil derivative I in aqueous sodium hydroxide solution at room temperature, whereby equivalent amounts of the uracil derivative and of sodium hydroxide are used. The solid salt can then be isolated by precipitation with a suitable inert solvent or by evaporation of the solvent. A further embodiment comprises introducing an aqueous solution of an alkali metal salt of the uracil derivative I into an aqueous solution of a salt which contains a metal cation other than an alkali metal cation, whereby the second metal salt of the uracil derivative is produced. This embodiment serves in general for the manufacture of uracil metal salts which are insoluble in water.

The compounds of formula I obtained as well as their salts can be isolated and purified according to methods known per se. Further, it is familiar to the person skilled in the art in which sequence certain reactions under process variants (b) and (d) to (n) are conveniently carried out in order to avoid possible, undesired competing reactions.

Insofar as no planned synthesis for the isolation of pure isomers is carried out, the product is obtained as a mixture of two or more isomers. The isomers can be separated according to methods known per se. If desired, pure optically active isomers can also be manufactured, for example, by synthesis from corresponding optically active starting materials.

The starting materials of formula II, which are novel, can be produced in a manner known per se, e.g. in accordance with the following Reaction Scheme 1 [methods (aa), (bb) and (cc)]:

REACTION SCHEME 1

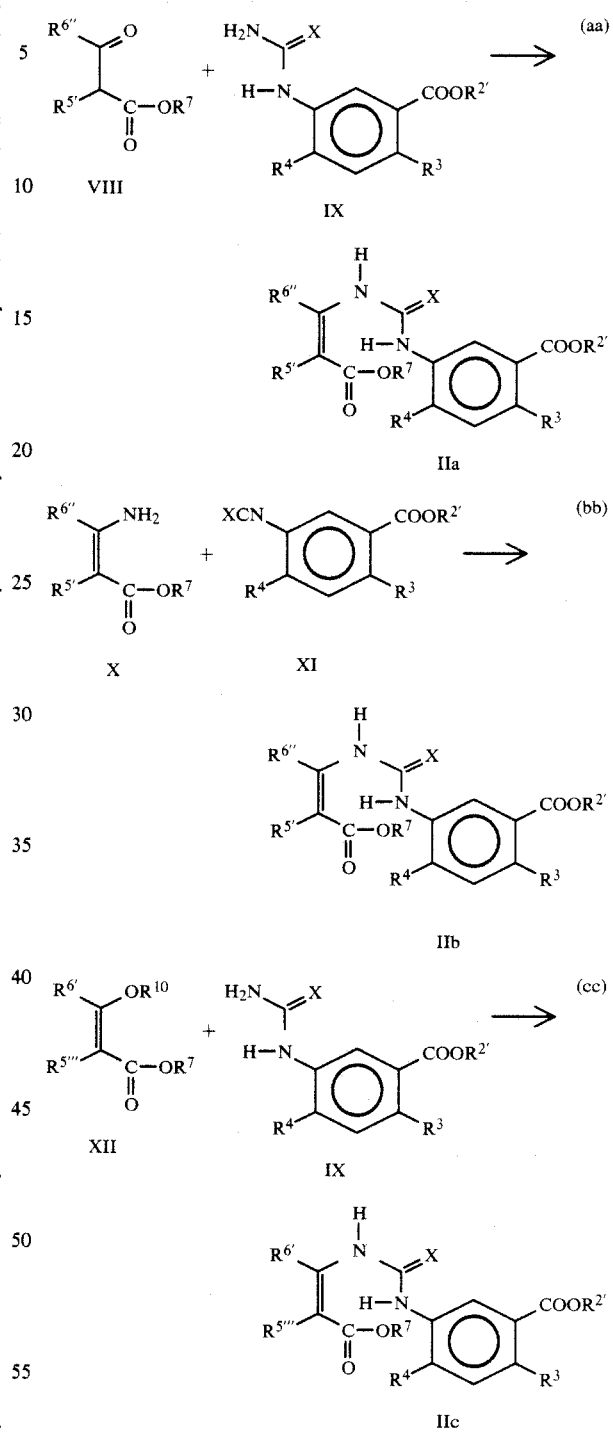

In the above Reaction Scheme $R^{2'}$, $R^3$, $R^4$, $R^{5'}$, $R^{6'}$, $R^7$ and X have the significances given above; $R^{5'''}$ signifies hydrogen or $C_{1-4}$-alkyl; $R^{6''}$ signifies $C_{1-4}$-alkyl, $C_{1-4}$-fluoroalkyl or together with $R^{5'}$ tri- or tetramethylene which is optionally modified as more precisely defined above; and $R^{10}$ signifies lower alkyl, preferably $C_{1-4}$-alkyl.

Method (aa) is conveniently carried out by reacting the compounds of formulae VIII and IX with each other in an essentially anhydrous diluent and in the presence of an acidic catalyst at elevated temperature. As diluents there come into consideration especially organic solvents which azeotrope with water, such as aromatics, e.g. benzene, toluene and xylenes; halogenated hydrocarbons such as methylene chloride, chloroform, carbon tetrachloride and chlorobenzene; and aliphatic and cyclic ethers such as 1,2-dimethoxyethane, tetrahydrofuran and dioxan, and as acidic catalysts there come into consideration especially strong mineral acids such as sulphuric acid and hydrochloric acid; organic acids such as p-toluenesulphonic acid; phosphorus-containing acids such as orthophosphoric acid and polyphosphoric acid; and acidic cation exchangers such as "Amberlyst 15" (Fluka). The reaction is generally carried out in a temperature range of about 70° C. to 120° C., preferably at the reflux temperature of the reaction mixture. Under these reaction conditions the desired rapid removal of the water formed in the reaction is achieved.

The reaction according to method (bb) is conveniently carried out in the presence of an essentially anhydrous aprotic organic solvent such as an aliphatic or cyclic ether, e.g. diethyl ether, 1,2-dimethoxyethane, tetrahydrofuran or dioxan, an aliphatic or aromatic hydrocarbon, e.g. n-hexane, benzene, toluene or a xylene; or a halogenated aliphatic hydrocarbon, e.g. methylene chloride, chloroform, carbon tetrachloride or 1,2-dichloroethane, as well as, if desired, in the presence of an organic tertiary base such as triethylamine or pyridine, whereby the latter can serve not only as the solvent but also as the base, or a metal hydride base, such as sodium or potassium hydride. The reaction temperatures are preferably in the range of about room temperature to 50° C., whereby the reaction is especially preferably carried out at room temperature.

The reaction according to method (cc) is conveniently carried out in an inert, water-miscible organic solvent such as an aliphatic or cyclic ether, e.g. 1,2-dimethoxyethane, tetrahydrofuran or dioxan, or a lower alkanol such as ethanol, at temperatures between 50° C. and 100° C., preferably at the reflux temperature of the reaction mixture, or in an aromatic solvent such as benzene, toluene or a xylene, in the presence of an acid catalyst, such as hydrochloric acid or p-toluenesulphonic acid, at temperatures between 50° C. and 100° C., preferably 60° C. to 80° C.

The compounds of formulae Ia–Ig which serve as the starting materials in process variants (b), (d)–(h) and (j)–(n) are sub-groups of compounds of formula I.

The starting materials of formula III which are required in process variant (c) can be produced in a manner known per se, in particular in accordance with the following Reaction Scheme 2:

REACTION SCHEME 2

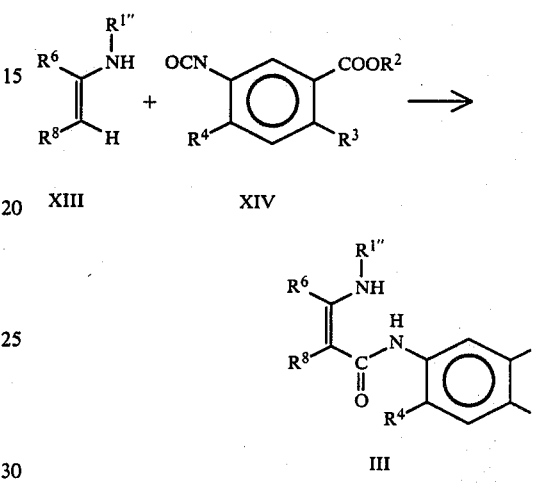

In the above Reaction Scheme $R^{1''}$, $R^2$, $R^3$, $R^4$, $R^6$ and $R^8$ have the significances given above, whereby $R^8$ as ($C_{1-4}$-alkoxy)carbonyl preferably signifies tert.butoxycarbonyl. The reaction of the compounds of formulae XIII and XIV is preferably effected in an aprotic organic solvent such as an aliphatic or cyclic ether, e.g. diethyl ether or tetrahydrofuran, at temperatures between 0° C. and 50° C., preferably at room temperature. As a rule the reactants react spontaneously and exothermically with each other.

The starting materials of formula VI which are required in process variant (i) can also be produced in a manner known per se, in particular in accordance with the following Reaction Scheme 3:

REACTION SCHEME 3

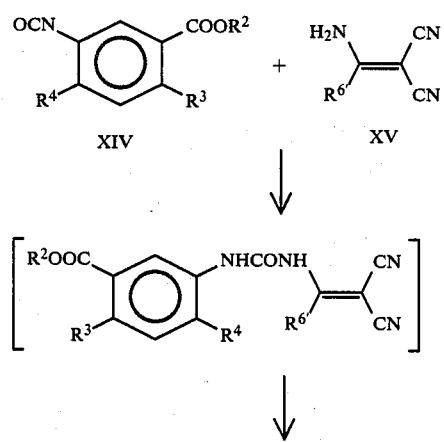

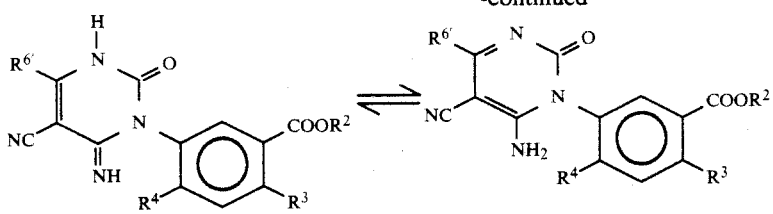

-continued

VI

In the above Reaction Scheme $R^3$, $R^3$, $R^4$ and $R^{6'}$ have the significances given above.

The reaction of the compounds of formulae XIV and XV with one another can be carried out conveniently in the presence of a diluent, especially an aprotic, polar organic diluent, such as dimethylformamide or dimethyl sulphoxide, as well as in the presence of a base, such as sodium hydride. The reaction is preferably carried out at temperatures between 20° C. and 50° C. In order to isolate the product of formula VI the mixture is acidified, whereby the free 5-cyanocytosine of formula VI is liberated, for example from the corresponding sodium salt.

The remaining starting materials or reagents which are involved in process variants (a)–(n) and methods (aa)–(cc) as well as the starting materials or reagents which are involved in Reaction Schemes 2 and 3 are either known or can be produced according to methods known per se.

The compounds of formula I' in accordance with the invention possess herbicidal properties and are suitable for the control of weeds, including weed grasses, especially *Setaria faberii, Digitaria sanguinalis, Poa annua, Chenopodium album, Amaranthus retroflexus, Abutilon theopharasti, Sinapsis alba* and *Datura stramonium*, in diverse economical plant cultivations, especially in cotton and soya cultivations. Moreover, the compounds are not only pre-emergence, but also post-emergence herbicides.

Certain compounds of formula II also possess herbicidal properties and can be used for the control of weed grasses and weeds, especially of the above-mentioned, in a similar manner to the compounds I'. The novel compounds II form a further object of the present invention. In view of their especially notable herbicidal activity isopropyl 2-chloro-4-fluoro-5-{3-[2-(ethoxycarbonyl)-1-cyclo-hexen-1-yl]ureido}-benzoate and isopropyl 2-chloro-4-fluoro-5-{3-[2-(ethoxycarbonyl)-1-methylpropenyl]ureido}-benzoate represent preferred compounds of formula II.

Under practical conditions a concentration of 0.01–6,0 kg of active substance of formula I' or II/ha, preferably 0.05–2,0 kg of active substance of formula I' or II/ha, is sufficient to produce the desired herbicidal effect, whereby the compounds of formula I' are generally significantly more active than the herbicidally active compounds of formula II. The concentration range 0.05–1.5 kg of active substance of formula I' or II/ha is especially preferred.

The weed control composition in accordance with the invention is characterized in that it contains an effective amount of at least one compound of formula I' or II, as defined above, as well as formulation adjuvants. The composition conveniently contains at least one of the following formulation adjuvants: solid carrier substances; solvents or dispersion media; tensides (wetting and emulsifying agents); dispersing agents (without tenside action); and stabilizers. With the use of these and other adjuvants these compounds, namely the herbicidally active substances, can be converted into the usual formulations such as dusts, powders, granulates, solutions, emulsions, suspensions, emulsifiable concentrates, pastes and the like.

The compounds of formula I' and II are generally insoluble in water and can be formulated according to methods which are usual for water-insoluble compounds using the respective formulation adjuvants. The manufacture of the compositions can be carried out in a manner known per se, e.g. by mixing the particular active substance with solid carrier substances, by dissolution or suspension in suitable solvents or dispersion media, if necessary using tensides as wetting or emulsifying agents and/or dispersing agents, by diluting pre-prepared emulsifiable concentrates with solvents or dispersion media etc.

As solid carrier substances there essentially come into consideration: natural mineral substances such as chalk, dolomite, limestone, aluminas and silicic acid and salts thereof (for example siliceous earth, kaolin, bentonite, talc, attapulgite and montmorillonite); synthetic mineral substances such as highly dispersible silicic acid, aluminium oxide and silicates; organic substances such as cellulose, starch, urea and synthetic resins; and fertilizers such as phosphates and nitrates, whereby such carrier substances can be present e.g. as powders or as granulates.

As solvents or dispersion media there essentially come into consideration: aromatics such as benzene, toluene, xylenes and alkylnaphthalenes; chlorinated aromatics and chlorinated aliphatic hydrocarbons such as chlorobenzenes, chloroethylenes and methylene chloride; aliphatic hydrocarbons such as cyclohexane and paraffins, e.g. petroleum fractions; alcohols such as butanol and glycol, as well as their ethers and esters; ketones such as acetone, methyl ethyl ketone, methyl isobutyl ketone and cyclohexanone; and strongly polar solvents or dispersion media such as dimethylformamide, N-methylpyrrolidone and dimethyl sulphoxide, such solvents preferably having flash points of at least 30° C. and boiling points of at least 50° C., and water. Among the solvents or dispersion media there also come into consideration so-called liquified gaseous extenders or carrier substances, which are those products which are gaseous at room temperature and under normal pressure. Examples of such products are especially aerosol propellants such as halogenated hydrocarbons, e.g. dichlorodifluoromethane. If the weed control composition in accordance with the invention is present in the form of a pressurized pack, then a solvent is conveniently used in addition to the propellant.

The tensides (wetting and emulsifying agents) can be non-ionic compounds such as condensation products of fatty acids, fatty alcohols or fatty-substituted phenols with ethylene oxide; fatty acid esters and ethers of sugars or polyvalent alcohols; the products which are obtained from sugars or polyvalent alcohols by condensation with ethylene oxide; block polymers of ethylene oxide and propylene oxide; or alkyldimethylamine oxides.

The tensides can also be anionic compounds such as soaps; fatty sulphate esters, e.g. dodecyl sodium sulphate, octadecyl sodium sulphate and cetyl sodium sulphate; alkyl sulphonates, aryl sulphonates and fatty-aromatic sulphonates such as alkylbenzene sulphonates, e.g. calcium dodecylbenzenesulphonate, and butylnaphthalene sulphonates; and more complex fatty sulphonates, e.g. the amide condensation products of oleic acid and N-methyltaurine and the sodium sulphonate of dioctyl succinate.

Finally, the tensides can be cationic compounds such as alkyldimethylbenzylammonium chlorides, dialkyldimethylammonium chlorides, alkyltrimethylammonium chlorides and ethoxylated quaternary ammonium chlorides.

As dispersing agents (without tenside action) there essentially come into consideration; lignin, sodium and ammonium salts of lignin sulphonic acids, sodium salts of maleic anhydride-diisobutylene copolymers, sodium and ammonium salts of sulphonated polycondensation products of naphthalene and formaldehyde, and sulphite lyes.

As dispersing agents, which are especially suitable as thickening or anti-settling agents, there can be used e.g. methylcellulose, carboxymethylcellulose, hydroxyethylcellulose, polyvinyl alcohol, alginates, caseinates and blood albumin.

Examples of suitable stabilizers are acid-binding agents, e.g. epichlorohydrin, phenyl glycidyl ether and soya epoxides; antioxidants, e.g. gallic acid esters and butylhydroxytoluene; UV-absorbers, e.g. substituted benzophenones, diphenylacrylonitrile acid esters and cinnamic acid esters; and deactivators, e.g. salts of ethylenediaminotetraacetic acid and polyglycols.

The weed control compositions in accordance with the invention can contain, in addition to the active substances in accordance with the invention, synergists and other active substances, e.g. insecticides, acaricides, fungicides, plant growth regulators and fertilizers. Such combination compositions are suitable for intensifying the activity or for broadening the spectrum of activity.

The weed control compositions in accordance with the invention generally contain between 0.01 and 95 weight percent, preferably between 0.5 and 75 weight percent, of one or more compounds of formula I' or II as the active substance(s). They can be present e.g. in a form which is suitable for storage and transport. In such formulations, e.g. emulsifiable concentrates, the active substance concentration is normally in the higher range, preferably between 1 and 50 weight percent, especially between 10 and 20 weight percent. These formulations can then be diluted, e.g. with the same or different inert substances, to give active substance concentrations which are suitable for practical use, i.e. preferably about 0.01 to 10 weight percent, especially about 0.5 to 5 weight percent. The active substance concentrations can, however, also be smaller or greater.

As mentioned above, the manufacture of the weed control compositions in accordance with the invention can be carried out in a manner known per se.

For the manufacture of pulverous preparations the active substance, i.e. at least one compound of formula I' or II, can be mixed with a solid carrier substance, e.g. by grinding together; or the solid carrier substance can be impregnated with a solution or suspension of the active substance and then the solvent or dispersion medium can be removed by evaporation, heating or sucking-off under reduced pressure. By adding tensides or dispersing agents such pulverous preparations can be made readily wettable with water, so that they can be converted into aqueous suspensions which are suitable e.g. as spray compositions.

The compound of formula I' and II can also be mixed with a tenside and a solid carrier substance to form a wettable powder which is dispersible in water, or it can be mixed with a solid pre-granulated carrier substance to form a product in the form of a granulate.

When desired, the compound of formula I' or II can be dissolved in a water-immiscible solvent such as, for example, a high-boiling hydrocarbon, which conveniently contains dissolved emulsifying agent, so that the solution becomes self-emulsifying upon addition to water. Alternatively, the active substance can be mixed with an emulsifying agent and the mixture can then be diluted with water to the desired concentration. Moreover, the active substance can be dissolved in a solvent and thereafter the solution can be mixed with an emulsifying agent. Such a mixture can likewise be diluted with water to the desired concentration. In this manner there are obtained emulsifiable concentrates or ready-for-use emulsions.

The use of the weed control compositions in accordance with the invention, which forms a further object of the present invention, can be carried out according to usual application methods such as sprinkling, spraying, dusting, watering or scattering. The method in accordance with the invention for the control of weeds is characterized by treating the locus to be protected against weeds and/or the weeds with a compound or formula I' or II in accordance with the invention or with a weed control composition in accordance with the invention.

The following Examples serve to illustrate the invention in more detail.

I. Manufacture of the compounds of formula I:

EXAMPLE 1

A solution of 118.0 g of ethyl 2-chloro-5-{3-[2-(ethoxycarbonyl)-1-cyclopenten-1-yl]ureido}-benzoate in 800 ml of absolute 1,2-dimethoxyethane, is added dropwise while stirring at 20° C. during 10 minutes to a suspension of 7.7 g of sodium hydride in 800 ml of absolute 1,2-dimethoxyethane. The reaction mixture is subsequently stirred for 1 hour, treated with 20 ml of acetic acid and evaporated to dryness under reduced pressure. The residue is dissolved in 2 l of methylene chloride and washed twice with 1 l of water. The organic phase is dried over anhydrous sodium sulphate and evaporated up to crystallization. The residue is treated with 1 l of n-hexane and the crystals are filtered off under suction and rinsed with n-hexane. There is obtained ethyl 2-chloro-5-(1,2,4,5,6,7-hexahydro-2,4-dioxo-3H-cyclopenta[d]pyrimidin-3-yl)-benzoate, m.p. 178°–180° C.

In an analogous manner,
using ethyl 2-chloro-5-{3-[2-(ethoxycarbonyl)-1-cyclohexen-1-yl]ureido}-benzoate there is obtained ethyl 2-chloro-5-[1,4,5,6,7,8-hexahydro-2,4-dioxo-3(2H)-quinazolinyl]-benzoate, m.p. 196°–198° C., using isopropyl 2-chloro-4-fluoro-5-{3-[2-(ethoxycarbonyl)-1-cyclopenten-1-yl]ureido}-benzoate there is obtained isopropyl 2-chloro-4-fluoro-5-(1,2,4,5,6,7-hexahydro-2,4-dioxo-3H-cyclopenta[d]pyrimidin-3-yl)-benzoate, m.p. 204°–207° C., using isopropyl 2-chloro-4-fluoro-5-{3-[2-(ethoxycarbonyl)-1-cyclohexen-1-yl]ureido}-benzoate there is obtained isopropyl 2-chloro-4-fluoro-5-[1,4,5,6,7,8-hexahydro-2,4-dioxo-3(2H)-quinazolinyl]-benzoate, m.p. 203°–205° C., using ethyl 2-chloro-5-{3-[2-(ethoxycarbonyl)vinyl]ureido}-benzoate with sodium ethylate in ethanol there is obtained ethyl 2-chloro-5-[3,6-dihydro-2,6-dioxo-1(2H)-pyrimidinyl]-benzoate, m.p. 170°–172° C., using ethyl 2-chloro-5-{3-[2-(ethoxycarbonyl)-1-methyl-vinyl]ureido}-benzoate there is obtained ethyl 2-chloro-5-[3,6-dihydro-4-methyl-2,6-dioxo-1(2H)-pyrimidinyl]-benzoate, m.p. 220°–223° C., using isopropyl 2-chloro-4-fluoro-5-{3-[2-(ethoxycarbonyl)-1-methyl-vinyl]ureido}-benzoate with sodium isopropylate in isopropanol there is obtained isopropyl 2-chloro-4-fluoro-5-[3,6-dihydro-4-methyl-2,6-dioxo-1(2H)-pyrimidinyl]-benzoate, m.p. 134°–136° C., using isopropyl 2-chloro-4-fluoro-5-{3-[2-(methoxycarbonyl)propenyl]ureido}-benzoate with sodium isopropylate in an isopropanol/dimethylformamide mixture there is obtained isopropyl 2-chloro-4-fluoro-5-[3,6-dihydro-5-methyl-2,6-dioxo-1(2H)-pyrimidinyl]-benzoate, m.p. 170°–173° C., using ethyl 2-chloro-5-{3-[2-(ethoxycarbonyl)-1-methyl-propenyl]ureido}-benzoate there is obtained ethyl 2-chloro-5-[3,6-dihydro-4,5-dimethyl-2,6-dioxo-1(2H)-pyrimidinyl]-benzoate, m.p. 202°–204° C., using isopropyl 2-chloro-4-fluoro-5-{3-[2-(ethoxycarbonyl)-1-methylpropenyl]ureido}-benzoate with sodium isopropylate in an isopropanol/dimethylformamide mixture there is obtained isopropyl 2-chloro-4-fluoro-5-[3,6-dihydro-4,5-dimethyl-2,6-dioxo-1(2H)-pyrimidinyl]-benzoate, m.p. 155°–157° C., using ethyl 5-{3-[2-(ethoxycarbonyl)-1-cyclopenten-1-yl]ureido}-2-nitrobenzoate with sodium ethylate in ethanol there is obtained ethyl 2-nitro-5-(1,2,4,5,6,7-hexahydro-2,4-dioxo-3H-cyclopenta[d]pyrimidin-3-yl)-benzoate, m.p. 205°–208° C., using isopropyl 2-chloro-4-fluoro-5-{3-[4-(methoxycarbonyl)-2,5-dihydrothien-3-yl]ureido}-benzoate with sodium isopropylate in an isopropanol/dimethylformamide mixture there is obtained isopropyl 2-chloro-4-fluoro-5-{1,2,5,7-tetrahydro-2,4-dioxothieno[3,4-d]pyrimidin-3(4H)-yl}-benzoate, m.p. 180°–183° C., using ethyl 2-chloro-5-{3-[4-(methoxycarbonyl)-2,5-dihydro-thien-3-yl]ureido}-benzoate with sodium ethylate in ethanol there is obtained ethyl 2-chloro-5-{1,2,5,7-tetrahydro-2,4-dioxo-thieno[3,4-d]pyrimidin-3(4H)-yl}-benzoate, m.p. 194°–196° C., using isopropyl 2-chloro-4-fluoro-5-{3-[2-(methoxycarbonyl)-4,5-dihydro-thien-3-yl]ureido}-benzoate with sodium isopropylate in an isopropanol/dimethylformamide mixture there is obtained isopropyl 2-chloro-4-fluoro-5-{1,4,6,7-tetrahydro-2,4-dioxothieno[3,2-d]pyrimidin-3(2H)-yl}-benzoate, m.p. 252°–254° C., using isopropyl 2-chloro-4-fluoro-5-{3-[2-(ethoxycarbonyl)-2-fluoro-1-methylvinyl]ureido}-benzoate with sodium isopropylate in an isopropanol/dimethylformamide mixture there is obtained isopropyl 2-chloro-4-fluoro-5-[3,6-dihydro-5-fluoro-4-methyl-2,6-dioxo-1(2H)-pyrimidinyl]-benzoate, $^1$H-NMR (CDCl$_3$, 400 MHz) 9.99 ppm (s, 1H), 7.84 ppm (d, 1H), 7.37 ppm (d, 1H), 5.26 ppm (m, 1H), 2.18 ppm (d, 3H), 1.38 ppm (d, 3H), 1.36 ppm (d, 3H), using isopropyl 2-chloro-4-fluoro-5-{3-[2-(ethoxycarbonyl)-1-propylvinyl]ureido}-benzoate with sodium isopropylate in isopropanol there is obtained isopropyl 2-chloro-4-fluoro-5-[3,6-dihydro-4-propyl-2,6-dioxo-1(2H)-pyrimidinyl]-benzoate, m.p. 192°–193° C., using isopropyl 2-chloro-4-fluoro-5-{3-[2-(ethoxycarbonyl)-1-ethylvinyl]ureido}-benzoate with sodium isopropylate in isopropanol there is obtained isopropyl 2-chloro-4-fluoro-5-[3,6-dihydro-4-ethyl-2,6-dioxo-1(2H)-pyrimidinyl]-benzoate, m.p. 121°–124° C., using isopropyl 2-chloro-4-fluoro-5-{3-[2-(ethoxycarbonyl)-1-methyl-1-butenyl]ureido}-benzoate with sodium isopropylate in an isopropanol/dimethylformamide mixture there is obtained isopropyl 2-chloro-4-fluoro-5-[3,6-dihydro-5-ethyl-4-methyl-2,6-dioxo-1(2H)-pyrimidinyl]-benzoate, m.p. 176°–178° C., using isopropyl 2-chloro-4-fluoro-5-{3-[2-(ethoxycarbonyl)-1-ethyl-1-propenyl]ureido}-benzoate with sodium isopropylate in an isopropanol/dimethylformamide mixture there is obtained isopropyl 2-chloro-4-fluoro-5-[3,6-dihydro-4-ethyl-5-methyl-2,6-dioxo-1(2H)-pyrimidinyl]-benzoate, m.p. 192°–194° C., using isopropyl 2,4-difluoro-5-{3-[2-(ethoxycarbonyl)-1-cyclopenten-1-yl]ureido}-benzoate with sodium isopropylate in isopropanol there is obtained isopropyl 2,4-difluoro-5-(1,2,4,5,6,7-hexahydro-2,4-dioxo-3H-cyclopenta[d]pyrimidin-3-yl)-benzoate, m.p. 231°–234° C., using isopropyl 2,4-dichloro-5-{3-[2-(ethoxycarbonyl)-1-cyclopenten-1-yl]ureido}-benzoate with sodium isopropylate in isopropanol there is obtained isopropyl 2,4-dichloro-5-(1,2,4,5,6,7-hexahydro-2,4-dioxo-3H-cyclopenta[d]pyrimidin-3-yl)-benzoate, m.p. 186°–189° C., using isopropyl 2-bromo-4-chloro-5-{3-[2-(ethoxycarbonyl)-1-cyclopenten-1-yl]ureido}-benzoate with sodium isopropylate in isopropanol there is obtained isopropyl 2-bromo-4-chloro-5-(1,2,4,5,6,7-hexahydro-2,4-dioxo-3H-cyclopenta[d]pyrimidin-3-yl)-benzoate, m.p. 208°–210° C., using isopropyl 2-bromo-4-fluoro-5-{3-[2-(ethoxycarbonyl)-1-cyclopenten-1-yl]ureido}-benzoate with sodium isopropylate in isopropanol there is obtained isopropyl 2-bromo-4-fluoro-5-(1,2,4,5,6,7-hexahydro-2,4-dioxo-3H-cyclopenta[d]pyrimidin-3-yl)-benzoate, m.p. 214°–216° C., using isopropyl 2,4-dibromo-5-{3-[2-(ethoxycarbonyl)-1-cyclopenten-1-yl]ureido}-benzoate with sodium isopropylate in isopropanol there is obtained isopropyl 2,4-dibromo-5-(1,2,4,5,6,7-hexahydro-2,4-dioxo-3H-cyclopenta[d]pyrimidin-3-yl)-benzoate, m.p. 223°–226° C., using isopropyl 2-chloro-4-fluoro-5-{3-[3-(ethoxycarbonyl)-4,5-dihydro-furan-2-yl]ureido}-benzoate with sodium isopropylate in an isopropanol/dimethylformamide mixture there is obtained isopropyl 2-chloro-4-fluoro-5-{1,2,5,6-tetrahydro-2,4-dioxo-furo[2,3-d]pyrimidin-3(4H)-yl}-benzoate, m.p. 213°–215° C., using isopropyl 2-chloro-5-{3-[2-(ethoxycarbonyl)-1-methylvinyl]thioureido}-benzoate with sodium isopropylate in an isopropanol/dimethyllformamide mixture there is obtained isopropyl 2-chloro-5-[3,6-dihydro-4-methyl-6-oxo-2-thioxo-1(2H)-pyrimidinyl]-benzoate, using isopropyl 2-chloro-5-{3-[2-(ethoxycarbonyl)-1-trifluoromethylvinyl]thioureido}-benzoate with sodium isopropylate in an isopropanol/dimethylformamide mixture there is obtained isopropyl 2-chloro-5-[3,6-dihydro-4-trifluoromethyl-6-oxo-2-thioxo-1(2H)-pyrimidinyl]-benzoate, using isopropyl 2-chloro-5-{3-[2-(ethoxycarbonyl)-1-cyclopenten-1-yl]thioureido}-benzoate with sodium isopropylate in an isopropanol/dimethylformamide mixture there is obtained isopropyl 2-chloro-5-(1,2,4,5,6,7-hexahydro-4-oxo-2-thioxo-3H-cyclopenta[d]pyrimidin-3-yl)-benzoate.

EXAMPLE 2

A solution of 3.55 g of ethyl 3-amino-4,4,4-trifluorocrotonate in 50 ml of n-hexane is added dropwise with stirring and at 0°–3° C. during 15 minutes to 0.85 g of a 55% sodium hydride dispersion in 50 ml of dimethylformamide, and the mixture is stirred for a further 30 minutes. Then a solution of 5.0 g of isopropyl 2-chloro-4-fluoro-5-isocyanatobenzoate in 100 ml of n-hexane is added dropwise during 5 minutes with stirring and cooling. The temperature of the reaction mixture rises to 10° C., and the mixture is thereafter stirred for one hour at room temperature. The isopropyl 2-chloro-4-fluoro-5-{3-[2-(ethoxycarbonyl)-1-trifluoromethyl-vinyl]ureido}-benzoate which is formed as an intermediate is not isolated.

The pH of the mixture is adjusted to 4 by addition of concentrated acetic acid, the mixture is poured into 750 ml of water and the aqueous mixture is extracted with 300 ml of ethyl acetate. The organic phase is dried over anhydrous sodium sulphate and subsequently evaporated to dryness under reduced pressure, and the residue is recrystallized from diethyl ether/n-hexane. In this manner isopropyl 2-chloro-4-fluoro-5-[3,6-dihydro-4-trifluoromethyl-2,6-dioxo-1(2H)-pyrimidinyl]-benzoate, m.p. 127°–129° C., is obtained.

EXAMPLE 3

Ammonia is introduced with stirring into a solution of 7.5 g of ethyl 3-oxo-2,4,4,4-tetrafluorobutyrate in 20 ml of toluene at 75° C. up to saturation. Then the reaction mixture is heated using a water separator for 5 hours, during which ethyl 3-amino-2,4,4,4-tetrafluorocrotonate is formed as an intermediate.

The reaction mixture at 0° C. is added dropwise during 20 minutes to a stirred suspension of 1.62 g of a 55% sodium hydride dispersion in 80 ml of absolute dimethylformamide, and the whole is stirred at 0° C. for a further 15 minutes and thereafter cooled to −5° C. A solution of 9.56 g of isopropyl 2-chloro-4-fluoro-5-isocyanatobenzoate in 40 ml of n-hexane is added. The temperature of the reaction mixture rises to 10° C., and the mixture is then stirred for a further 3 hours at room temperature. The isopropyl 2-chloro-4-fluoro-5-{3-[2-(ethoxycarbonyl)-2-fluoro-1-trifluoromethyl-vinyl]-ureido}-benzoate which is formed as an intermediate is not isolated.

The reaction mixture is poured into 1.5 l of water containing 20 ml of 2N hydrochloric acid and the aqueous mixture is extracted twice with 200 ml amounts of ethyl acetate. The organic phase is washed with water, dried over anhydrous sodium sulphate and evaporated to dryness under reduced pressure. The residue is briefly stirred in 100 ml of diethyl ether and a solution of 5 g of sodium bicarbonate in 300 ml of water at 50° C. and cooled down. After separation of the aqueous phase the organic phase is shaken three times with a solution of 2.5 g of sodium bicarbonate in 100 ml of water, and then the combined aqueous solutions are acidified to pH 1 with 15 ml of concentrated hydrochloric acid and extracted with diethyl ether. The organic phase is then washed with water, dried over anhydrous sodium sulphate and evaporated to dryness under reduced pressure. Finally the residue is recrystallized from diethyl ether/n-hexane.

In this way isopropyl 2-chloro-4-fluoro-5-[3,6-dihydro-5-fluoro-4-trifluoromethyl-2,6-dioxo-1(2H)-pyrimidinyl]-benzoate, m.p. 102°–106° C., is obtained.

EXAMPLE 4

A solution of 1.80 g of ethyl 3-amino-2,4-difluorocrotonate in 20 ml of absolute dimethylformamide is added dropwise with stirring during 10 minutes to 0.48 g of a 55% sodium hydride dispersion in 25 ml of dimethylformamide at room temperature, and the mixture is stirred for a further 15 minutes. Thereafter 2.81 g of isopropyl 2-chloro-4-fluoro-5-isocyanatobenzoate are added, with the result that the temperature of the reaction mixture rises to 35° C. Then the mixture is stirred for a further two hours at room temperature. The isopropyl 2-chloro-4-fluoro-5-{3-[2-(ethoxycarbonyl)-2-fluoro-1-fluoromethyl-vinyl]ureido}-benzoate formed as an intermediate is not isolated.

The mixture is poured into 300 ml of water containing 5.5 ml of 2N hydrochloric acid, the aqueous mixture is extracted three times with 50 ml amounts of ethyl acetate and the combined organic phases are washed with water, dried over anhydrous sodium sulphate and evaporated under reduced pressure to dryness. The residue is purified by chromatography on a silica gel column using ethyl acetate/n-hexane (1:1) as the eluent and recrystallized from diethyl ether/n-hexane. Isopropyl 2-chloro-4-fluoro-5-[3,6-dihydro-5-fluoro-4-fluoromethyl-2,6-dioxo-1(2H)-pyrimidinyl]-benzoate, m.p. 171°–173° C., is obtained.

EXAMPLE 5

A solution of 50.2 g of ethyl 2-chloro-5-(1,2,4,5,6,7-hexahydro-2,4-dioxo-3H-cyclopenta[d]pyrimidin-3-yl)-benzoate in 300 ml of absolute 1,2-dimethoxyethane is added dropwise while stirring at 20° C. during 10 minutes to a suspension of 3.6 g of sodium hydride in 100 ml of absolute 1,2-dimethoxyethane. The reaction mixture is stirred for 1 hour, treated with 21.3 g of methyl iodide and stirred for a further 2 hours. The mixture is subsequently rendered neutral with 0.5 ml of acetic acid and evaporated to dryness under reduced pressure. The residue is dissolved in 500 ml of ethyl acetate, the solution shaken three times with 250 ml of water, and the organic phase is dried over anhydrous sodium sulphate and evaporated to dryness under reduced pressure. The residue is dissolved in 50 ml of hot methylene chloride, seeded, and treated with diethyl ether. There is obtained ethyl 2-chloro-5-(1,2,4,5,6,7-hexahydro-1-methyl-2,4-dioxo-3H-cyclopenta[d]pyrimidin-3-yl)-benzoate, m.p. 141°–143° C.

In an analogous manner,
using ethyl 2-chloro-5-[1,4,5,6,7,8-hexahydro-2,4-dioxo-3(2H)-quinazolinyl]-benzoate there is obtained ethyl 2-chloro-5-[1,4,5,6,7,8-hexahydro-1-methyl-2,4-dioxo-3(2H)-quinazolinyl]-benzoate, m.p. 108°–112° C., using isopropyl 2-chloro-4-fluoro-5-(1,2,4,5,6,7-hexahydro-2,4-dioxo-3H-cyclopenta[d]pyrimidin-3-yl)-benzoate there is obtained isopropyl 2-chloro-4-fluoro-5-(1,2,4,5,6,7-hexahydro-1-methyl-2,4-dioxo-3H-cyclopenta[d]pyrimidin-3-yl)-benzoate, m.p. 111°–113° C., using isopropyl 2-chloro-4-fluoro-5-[1,4,5,6,7,8-hexahydro-2,4-dioxo-3(2H)-quinazolinyl]-benzoate there is obtained isopropyl 2-chloro-4-fluoro-5-[1,4,5,6,7,8-hexahydro-1-methyl-2,4-dioxo-3(2H)-quinazolinyl]-benzoate, m.p. 113°–115° C., using ethyl 2-chloro-5-(1,2,4,5,6,7-hexahydro-2,4-dioxo-3H-cyclopenta[d]pyrimidin-3-yl)-benzoate and chlorodimethyl ether in dimethylformamide there is obtained ethyl 2-chloro-5-(1,2,4,5,6,7-hexahydro-1-methoxymethyl-2,4-dioxo-3H-cyclopenta[d]pyrimidin-3-yl)-benzoate, m.p. 103°–106° C., using ethyl 2-chloro-5-(1,2,4,5,6,7-hexahydro-2,4-dioxo-3H-cyclopenta[d]pyrimidin-3-yl)-benzoate and 3-bromo-1-propyne there is obtained ethyl 2-chloro-5-{1,2,4,5,6,7-hexahydro-1-(2-propynyl)-2,4-dioxo-3H-cyclopenta[d]pyrimidin-3-yl}-benzoate, m.p. 121°–123° C., using ethyl 2-chloro-5-[3,6-dihydro-2,6-dioxo-1(2H)-pyrimidinyl]-benzoate in dimethylformamide there is obtained ethyl 2-chloro-5-[3,6-dihydro-3-methyl-2,6-dioxo-1(2H)-pyrimidinyl]-benzoate, m.p. 147°–148° C., using ethyl 2-chloro-5-[3,6-dihydro-4-methyl-2,6-dioxo-1(2H)-pyrimidinyl]-benzoate there is obtained ethyl 2-chloro-5-[3,6-dihydro-3,4-dimethyl-2,6-dioxo-1(2H)-pyrimidinyl]-benzoate, m.p. 120°–122° C., using isopropyl 2-chloro-4-fluoro-5-[3,6-dihydro-4-methyl-2,6-dioxo-1(2H)-pyrimidinyl]-benzoate with sodium isopropylate in isopropanol there is obtained isopropyl 2-chloro-4-fluoro-5-[3,6-dihydro-3,4-dimethyl-2,6-dioxo-1(2H)-pyrimidinyl]-benzoate, $^1$H-NMR (CDCl$_3$, 60 MHz) 7.88 ppm (d, 1H), 7.38 ppm (d, 1H), 5.77 ppm (s, 1H), 5.30 ppm (m, 1H), 3.50 ppm (s, 3H), 2.36 ppm (s, 3H), 1.40 ppm (d, 6H), using isopropyl 2-chloro-4-fluoro-5-[3,6-dihydro-5-methyl-2,6-dioxo-1(2H)-pyrimidinyl]-benzoate in dimethylformamide there is obtained isopropyl 2-chloro-4-fluoro-5-[3,6-dihydro-3,5-dimethyl-2,6-dioxo-1(2H)-pyrimidinyl]-benzoate, m.p. 177°–180° C., using ethyl 2-chloro-5-[3,6-dihydro-4,5-dimethyl-2,6-dioxo-1(2H)-pyrimidinyl]-benzoate there is obtained ethyl 2-chloro-5-[3,6-dihydro-3,4,5-trimethyl-2,6-dioxo-1(2H)-pyrimidinyl]-benzoate, m.p. 159°–161° C., using isopropyl 2-chloro-4-fluoro-5-[3,6-dihydro-4,5-dimethyl-2,6-dioxo-1(2H)-pyrimidinyl]-benzoate in dimethylformamide there is obtained isopropyl 2-chloro-4-fluoro-5-[3,5-dihydro-3,4,5-trimethyl-2,6-dioxo-1(2H)-pyrimidinyl]-benzoate, m.p. 119°–120° C., using ethyl 2-nitro-5-(1,2,4,5,6,7-hexahydro-2,4-dioxo-3H-cyclopenta[d]pyrimidin-3-yl)-benzoate with sodium ethylate in ethanol there is obtained ethyl 2-nitro-5-(1,2,4,5,6,7-hexahydro-1-methyl-2,4-dioxo-3H-cyclopenta[d]pyrimidin-3-yl)-benzoate, m.p. 188°–190° C., using isopropyl 2-chloro-4-fluoro-5-{1,2,5,7-tetrahydro-2,4-dioxo-thieno[3,4-d]pyrimidin-3(4H)-yl}-benzoate in dimethylformamide there is obtained isopropyl 2-chloro-4-fluoro-5-{1,2,5,7-tetrahydro-1-methyl-2,4-dioxo-thieno[3,4-d]pyrimidin-3(4H)-yl}-benzoate, $^1$H-NMR (CDCl$_3$, 400 MHz) 7.82 ppm (d, 1H), 7.35 ppm (d, 1H), 5.23 ppm (m, 1H), 4.24 ppm (m, 2H), 4.09 ppm (m, 2H), 3.45 ppm (s, 3H), 1.36 ppm (d, 6H), using ethyl 2-chloro-5-{1,2,5,7-tetrahydro-2,4-dioxo-thieno[3,4-d]pyrimidin-3(4H)-yl}-benzoate in dimethylformamide there is obtained ethyl 2-chloro-5-{1,2,5,7-tetrahydro-1-methyl-2,4-dioxo-thieno[3,4-d]pyrimidin-3(4H)-yl}-benzoate, m.p. 203°–206° C., using isopropyl 2-chloro-4-fluoro-5-{1,4,6,7-tetrahydro-2,4-dioxo-thieno[3,2-d]pyrimidin-3(2H)-yl}-benzoate there is obtained isopropyl 2-chloro-4-fluoro-5-{1,4,6,7-tetrahydro-1-methyl-2,4-dioxo-thieno[3,2-d]pyrimidin-3(2H)-yl}-benzoate, m.p. 156°–158° C., using isopropyl 2-chloro-4-fluoro-5-[3,6-dihydro-5-fluoro-4-methyl-2,6-dioxo-1(2H)-pyrimidinyl]-benzoate and dimethyl sulphate in dimethylformamide there is obtained isopropyl 2-chloro-4-fluoro-5-[3,6-dihydro-3,4-dimethyl-5-fluoro-2,6-dioxo-1(2H)-pyrimidinyl]-benzoate, m.p. 112°–115° C., using isopropyl 2-chloro-4-fluoro-5-[3,6-dihydro-4-propyl-2,6-dioxo-1(2H)-pyrimidinyl]-benzoate and dimethyl sulphate with sodium isopropylate in isopropanol there is obtained isopropyl 2-chloro-4-fluoro-5-[3,6-dihydro-3-methyl-4-propyl-2,6-dioxo-1(2H)-pyrimidinyl]-benzoate, $^1$H-NMR (CDCl$_3$, 400 MHz) 7.83 ppm (d, 1H), 7.34 ppm (d, 1H), 5.73 ppm (s, 1H), 5.23 ppm (m, 1H), 3.45 ppm (s, 3H), 2.53 ppm (t, 2H), 1.72 ppm (m, 2H), 1.36 ppm (d, 6H), 1.10 ppm (t, 3H), using isopropyl 2-chloro-4-fluoro-5-[4-ethyl-3,6-dihydro-2,6-dioxo-1(2H)-pyrimidinyl]-benzoate and dimethyl sulphate with sodium isopropylate in isopropanol there is obtained isopropyl 2-chloro-4-fluoro-5-[3,6-dihydro-4-ethyl-3-methyl-2,6-dioxo-1(2H)-pyrimidinyl]-benzoate, $^1$H-NMR (CDCl$_3$, 400 MHz) 7.84 ppm (d, 1H), 7.34 ppm (d, 1H), 5.75 ppm (s, 1H), 5.25 ppm (m, 1H), 3.45 ppm (s, 3H), 2.61 ppm (m, 2H), 1.36 ppm (d, 6H), 1.31 ppm (t, 3H), using isopropyl 2-chloro-4-fluoro-5-[3,6-dihydro-5-ethyl-4-methyl-2,6-dioxo-1(2H)-pyrimidinyl]-benzoate and dimethyl sulphate in dimethylformamide there is obtained isopropyl 2-chloro-4-fluoro-5-[3,6-dihydro-5-ethyl-3,4-dimethyl-2,6-dioxo-1(2H)-pyrimidinyl]-benzoate, $^1$H-NMR (CDCl$_3$, 400 MHz) 7.83 ppm (d, 1H), 7.33 ppm (d, 1H), 5.23 ppm (m, 1H), 3.48 ppm (s, 3H), 2.51 ppm (m, 2H), 2.34 ppm (s, 3H), 1.35 ppm (2xd, 6H), 1.09 ppm (t, 3H), using isopropyl 2-chloro-4-fluoro-5-[3,6-dihydro-4-ethyl-5-methyl-2,6-dioxo-1(2H)-pyrimidinyl]-benzoate and dimethyl sulphate in dimethylformamide there is obtained isopropyl 2-chloro-4-fluoro-5-[3,6-dihydro-4-ethyl-3,5-dimethyl-2,6-dioxo-1(2H)-pyrimidinyl]-benzoate, $^1$H-NMR (CDCl$_3$, 400 MHz) 7.82 ppm (d, 1H), 7.33 ppm (d, 1H), 5.23 ppm (m, 1H), 3.51 ppm (s, 3H), 2.71 ppm (m, 2H), 2.04 ppm (s, 3H), 1.35 ppm (d, 6H), 1.28 ppm (t, 3H), using isopropyl 2-chloro-4-fluoro-5-[3,6-dihydro-2,6-dioxo-4-trifluoromethyl-1(2H)-pyrimidinyl]-benzoate and dimethyl sulphate in dimethylformamide there is obtained isopropyl 2-chloro-4-fluoro-5-[3,6-dihydro-3-methyl-4-trifluoromethyl-2,6-dioxo-1(2H)-pyrimidinyl]benzoate, $^1$H-NMR (CDCl$_3$, 400 MHz) 7.84 ppm (d, 1H), 7.37 ppm (d, 1H), 6.38 ppm (s, 1H), 5.25 ppm (m, 1H), 3.57 ppm (d, 3H), 1,36 ppm (d, 6H), using isopropyl 2-chloro-4-fluoro-5-[5-cyano-3,6-dihydro-2,6-dioxo-1(2H)-pyrimidinyl]-benzoate and dimethyl sulphate in dimethylformamide there is obtained isopropyl 2-chloro-4-fluoro-5-[5-cyano-3,6-dihyddro-3-methyl-2,6-dioxo-1(2H)-pyrimidinyl]-benzoate, $^1$H-NMR (CDCl$_3$, 400 MHz) 8.00 ppm (s, 1H), 7.83 ppm (d, 1H), 7.38 ppm (d, 1H), 5.25 ppm (m, 1H), 3.55 ppm (s, 3H), 1.37 ppm (2xd, 6H), using isopropyl 2-chloro-4-fluoro-5-[5-cyano-3,6-dihydro-4-methyl-2,6-dioxo-1(2H)-pyrimidinyl]-benzoate and dimethyl sulphate in dimethylformamide there is obtained isopropyl 2-chloro-4-fluoro-5-[5-cyano-3,6-dihydro-3,4-dimethyl-2,6-dioxo-1(2H)-pyrimidinyl]-benzoate, m.p. 171°–173° C., using isopropyl 2-chloro-4-fluoro-5-[3,6-dihydro-5-fluoro-4-trifluoromethyl-2,6-dioxo-1(2H)-pyrimidinyl]-benzoate and dimethyl sulphate in dimethylformamide there is obtained isopropyl 2-chloro-4-fluoro-5-[3,6-dihydro-5-fluoro-3-methyl-4-trifluoromethyl-2,6-dioxo-1(2H)-pyrimidinyl]-benzoate, m.p. 66°–68° C., using isopropyl 2,4-difluoro-5-(1,2,4,5,6,7-hexahydro-2,4-dioxo-3H-cyclopenta[d]pyrimidin-3-yl)-benzoate and dimethyl sulphate with sodium isopropylate in isopropanol there is obtained isopropyl 2,4-difluoro-5-(1,2,4,5,6,7-hexahydro-1-methyl-2,4-dioxo-3H-cyclopenta[d]pyrimidin-3-yl)-benzoate, m.p. 112°–115° C., using isopropyl 2,4-dichloro-5-(1,2,4,5,6,7-hexahydro-2,4-dioxo-3H-cyclopenta[d]pyrimidin-3-yl)-benzoate and dimethyl sulphate with sodium isopropylate in isopropanol there is obtained isopropyl 2,4-dichloro-5-(1,2,4,5,6,7-hexahydro-1-methyl-2,4-dioxo-3H-cyclopenta[d]pyrimidin-3-yl)-benzoate, $^1$H-NMR (CDCl$_3$, 400 MHz, 7.78 ppm (s, 1H), 7.65 ppm (s, 1H), 5.23 ppm (m, 1H), 3.42 ppm (s, 3H), 2.96 ppm (m, 2H), 2.82 ppm (m, 2H), 2.17 ppm (m, 2H), 1.35 ppm (d, 6H), using isopropyl 2-bromo-4-chloro-5-(1,2,4,5,6,7-hexahydro-2,4-dioxo-3H-cyclopenta[d]pyrimidin-3-yl)-benzoate and dimethyl sulphate with sodium isopropylate in isopropanol there is obtained isopropyl 2-bromo-4-chloro-5-(1,2,4,5,6,7-hexahydro-1-methyl-2,4-dioxo-3H-cyclopenta[d]pyrimidin-3-yl)-benzoate, $^1$H-NMR (CDCl$_3$, 400 MHz) 7.86 ppm (s, 1H), 7.74 ppm (s, 1H), 5.23 ppm (m, 1H), 3.42 ppm (s, 3H), 2.96 ppm (m, 2H), 2.82 ppm (m, 2H), 2.18 ppm (m, 2H), 1.35 ppm (d, 6H), using isopropyl 2-bromo-4-fluoro-5-(1,2,4,5,6,7-hexahydro-2,4-dioxo-3H-cyclopenta[d]pyrimidin-3-yl)-benzoate and dimethyl sulphate with sodium isopropylate in isopropanol there is obtained isopropyl 2-bromo-4-fluoro-5-(1,2,4,5,6,7-hexahydro-1-methyl-2,4-dioxo-3H-cyclopenta-[d]pyrimidin-3-yl)-benzoate, m.p. 116°–120° C., using isopropyl 2,4-dibromo-5-(1,2,4,5,6,7-hexahydro-2,4-dioxo-3H-cyclopenta[d]pyrimidin-3-yl)-benzoate and dimethyl sulphate with sodium isopropylate in isopropanol there is obtained isopropyl 2,4-dibromo-5-(1,2,4,5,6,7-hexahydro-1-methyl-2,4-dioxo-3H-cyclopenta[d]pyrimidin-3-yl)-benzoate, $^1$H-NMR (CDCl$_3$, 400 MHz) 8.03 ppm (s, 1H), 4.72 ppm (s, 1H), 5.23 ppm (m, 1H), 2.96 ppm (m, 2H), 2.83 ppm (m, 2H), 2.17 ppm (m, 2H), 1.35 ppm (d, 6H), using isopropyl 2-chloro-4-fluoro-5-[3,6-dihydro-5-fluoro-4-fluoromethyl-2,6-dioxo-1(2H)-pyrimidinyl]-benzoate and dimethyl sulphate in dimethylformamide there is obtained isopropyl 2-chloro-4-fluoro-5-[3,6-dihydro-5-fluoro-4-fluoromethyl-3-methyl-2,6-dioxo-1(2H)-pyrimidinyl]-benzoate, m.p. 85°–89° C., using isopropyl 2-chloro-4-fluoro-5-(1,2,5,6-tetrahydro-2,4-dioxo-furo[2,3-d]pyrimidin-3(4H)-yl)-benzoate there is obtained isopropyl 2-chloro-4-fluoro-5-{1,2,5,6-tetrahydro-1-methyl-2,4-dioxo-furo[2,3-d]pyrimidin-3(4H)-yl}-benzoate, m.p. 170°–173° C.

EXAMPLE 6

A solution of 3.6 g of isopropyl 2-chloro-4-fluoro-5-(1,2,4,5,6,7-hexahydro-2,4-dioxo-3H-cyclopenta[d]pyrimidin-3-yl)-benzoate in 50 ml of absolute dimethylformamide is stirred at room temperature for 2 hours with 0.43 g of a 55% sodium hydride dispersion. A solution of 0.93 g of acetyl chloride in 10 ml of absolute dimethylformamide is subsequently added dropwise during 10 minutes and the mixture is stirred for 2 hours. The reaction mixture is dissolved in 100 ml of ethyl acetate and the solution is washed thoroughly with water. The organic phase is dried over anhydrous sodium sulphate and evaporated to dryness. The residue is purified by chromatography on a silica gel column using methylene chloride/ethyl acetate (3:1) as the eluent. There is obtained isopropyl 2-chloro-4-fluoro-5-(1,2,4,5,6,7-hexahydro-1-acetyl-2,4-dioxo-3H-cyclopenta[d]pyrimidin-3-yl)-benzoate, $^1$H-NMR (CDCl$_3$, 400 MHz) 7.86 ppm (d, 1H), 7.37 ppm (d, 1H), 5.24 ppm (m, 1H), 3.13 ppm (m, 2H), 2.75 ppm (m, 2H), 2.68 ppm (s, 3H), 2.12 ppm (m, 2H), 1.36 ppm (d, 6H).

In an analogous maner, using isopropyl 2-chloro-4-fluoro-5-(1,2,4,5,6,7-hexahydro-2,4-dioxo-3H-cyclopenta[d]pyrimidin-3-yl)-benzoate and methyl chloroformate there is obtained isopropyl 2-chloro-4-fluoro-5-(1,2,4,5,6,7-hexahydro-1-methoxycarbonyl-2,4-dioxo-3H-cyclopenta[d]pyrimidin-3-yl)-benzoate, $^1$H-NMR (CDCl$_3$, 400 MHz) 7.84 ppm (d, 1H), 7.35 ppm (d, 1H), 5.24 ppm (m, 1H), 4.03 ppm (s, 3H), 3.02 ppm (m, 2H), 2.79 ppm (m, 2H), 2.16 ppm, (m, 2H), 1.36 ppm (d, 6H), using isopropyl 2-chloro-4-fluoro-5-[3,6-dihydro-4-methyl-2,6-dioxo-1(2H)-pyrimidinyl]-benzoate there is obtained isopropyl 2-chloro-4-fluoro-5-[3-acetyl-3,6-dihydro-4-methyl-2,6-dioxo-1(2H)-pyrimidinyl]-benzoate, m.p. 168°–170° C.

EXAMPLE 7

6.3 g of sulphuryl chloride are added dropwise with stirring to a solution of 15.0 g of isopropyl 2-chloro-4-fluoro-5-[3,6-dihydro-3,4-dimethyl-2,6-dioxo-1(2H)-pyrimidinyl]-benzoate in 100 ml of acetic acid at room temperature during 1 minute, during which the temperature rises to approx. 30° C. Then the reaction mixture is stirred for a further 15 minutes at room temperature and evaporated to dryness under reduced pressure. The residue is dissolved in ethyl acetate and the solution washed in turn with aqueous sodium bicarbonate solution and water. The organic phase is dried over anhydrous sodium sulphate and evaporated to dryness. The residue is recrystallized from methylene chloride/diethyl ether. Isopropyl 2-chloro-4-fluoro-5-[5-chloro-3,6-dihydro-3,4-dimethyl-2,6-dioxo-1(2H)-pyrimidinyl]-benzoate, m.p. 150°–153° C., is obtained.

In an analogous manner, using isopropyl 2-chloro-4-fluoro-5-[3,6-dihydro-4-methyl-2,6-dioxo-1(2H)-pyrimidinyl]-benzoate there is obtained isopropyl 2-chloro-4-fluoro-5-[5-chloro-3,6-dihydro-4-methyl-2,6-dioxo-1(2H)-pyrimidinyl]-benzoate, m.p. 198°–201° C.

EXAMPLE 8

A solution of 1.7 g of bromine in 20 ml of acetic acid is added dropwise with stirring to a solution of 3.4 g of isopropyl 2-chloro-4-fluoro-5-[3,6-dihydro-4-methyl-2,6-dioxo-1(2H)-pyrimidinyl]-benzoate in 20 ml of acetic acid at 25° C. during 25 minutes. The reaction mixture is stirred for a further hour and evaporated to dryness under reduced pressure. The residue is dissolved in diethyl ether and washed with aqueous sodium bicarbonate solution, thereafter with water. The organic phase is dried over anhydrous sodium sulphate and evaporated to dryness. The residue is recrystallized from diethyl ether/n-hexane. There is obtained isopropyl 2-chloro-4-fluoro-5-[5-bromo-3,6-dihydro-4-methyl-2,6-dioxo-1(2H)-pyrimidinyl]-benzoate, m.p. 187°–189° C.

In an analogous manner, using isopropyl 2-chloro-4-fluoro-5-[3,6-dihydro-3,4-dimethyl-2,6-dioxo-1(2H)-pyrimidinyl]-benzoate there is obtained isopropyl 2-chloro-4-fluoro-5-[5-bromo-3,6-dihydro-3,4-dimethyl-2,6-dioxo-1(2H)-pyrimidinyl]-benzoate, m.p. 127°–129° C.

EXAMPLE 9

1.50 g of isopropyl 2-chloro-4-fluoro-5-[3,6-dihydro-3,4-dimethyl-2,6-dioxo-1(2H)-pyrimidinyl]-benzoate in 10 ml of acetic acid are treated with 0.70 g of iodine and the reaction mixture is stirred for 1 hour at room temperature. Subsequently the reaction mixture is treated with 0.67 g of 100% nitric acid and stirred at room temperature for 3 hours. The reaction mixture is poured into 150 ml of ice/water and extracted with 100 ml of ethyl acetate. The organic phase is washed with 150 ml of water, thereafter with 150 ml of aqueous sodium bicarbonate solution and finally with 150 ml of saturated aqueous sodium bisulphite solution. The upper phase is dried over anhydrous sodium sulphate and evaporated to dryness under reduced pressure. The residue is recrystallized from methylene chloride/n-hexane. Isopropyl 2-chloro-4-fluoro-5-[3,6-dihydro-3,4-dimethyl-5-iodo-2,6-dioxo-1(2H)-pyrimidinyl]-benzoate, m.p. 147°–150° C., is obtained.

In an analogous manner.

using isopropyl 2-chloro-4-fluoro-5-[3,6-dihydro-4-methyl-2,6-dioxo-1(2H)-pyrimidinyl]-benzoate there is obtained isopropyl 2-chloro-4-fluoro-5-[3,6-dihydro-5-iodo-4-methyl-2,6-dioxo-1(2H)-pyrimidinyl]-benzoate, m.p. 211°–213° c.

EXAMPLE 10

5.0 g of isopropyl 2-chloro-4-fluoro-5-[3,6-dihydro-3,4-dimethyl-2,6-dioxo-1(2H)-pyrimidinyl]-benzoate and 5.7 g of chlorodimethyl ether are heated at 100° C. for 24 hours in an autoclave (approx. 8–9 atm.). After cooling the reaction mixture this is treated with methylene chloride and evaporated to dryness at 50° C. under reduced pressure. Isopropyl 2-chloro-4-fluoro-5-[5-chloromethyl-3,6-dihydro-3,4-dimethyl-2,6-dioxo-1(2H)-pyrimidinyl]-benzoate, which does not have to be purified for any further reactions, is obtained. $^1$H-NMR (CDCl$_3$, 400 MHz) 7.83 ppm (d, 1H), 7.34 ppm (d, 1H), 5.24 ppm (m, 1H), 4.64 ppm (d, 1H), 4.54 ppm (d, 1H), 3.52 ppm (s, 3H), 2.48 ppm (s,3H), 1.37 ppm (d, 3H), 1.35 ppm (d, 3H).

EXAMPLE 11

A solution of 3.5 g of isopropyl 2-chloro-4-fluoro-5-[3,6-dihydro-3,5-dimethyl-2,6-dioxo-1(2H)-pyrimidinyl]-benzoate in 100 ml of carbon tetrachloride is heated to reflux temperature while stirring for 1 hour with 1.8 g of N-bromosuccinimide and some dibenzoyl peroxide. The reaction mixture is irradiated with a 150 W bulb. The succinimide is filtered off under suction and the filtrate is evaporated to dryness under reduced pressure. The residue is purified by chromatography on a silica gel column using methylene chloride/ethyl acetate (7:1) as the eluent. There is obtained isopropyl 2-chloro-4-fluoro-5-[5-bromomethyl-3,6-dihydro-3-methyl-2,6-dioxo-1(2H)-pyrimidinyl]-benzoate, $^1$H-NMR (CDCl$_3$, 400 MHz) 7.84 ppm (d, 1H), 7.58 ppm (s, 1H), 7.36 ppm (d, 1H), 5.24 ppm (m, 1H), 4.35 ppm (d, 1H), 4.29 ppm (d, 1H), 3.48 ppm (s, 3H), 1.37 ppm (2d, 6H).

EXAMPLE 12

A solution of 1.14 g of isopropyl 2-chloro-4-fluoro-5-[5-chloromethyl-3,6-dihydro-3,4-dimethyl-2,6-dioxo-1(2H)-pyrimidinyl]-benzoate in 20 ml 1,2-dimethoxyethane is stirred at room temperature for 3 hours with a solution of 0.47 g of sodium bicarbonate in 10 ml of water. The solvent is evaporated off under reduced pressure and the residue is extracted with ethyl acetate. The organic phase is dried over anhydrous sodium sulphate and evaporated to dryness. The residue is purifed by chromatography on a silica gel column using methylene chloride/ethyl acetate (2:1) as the eluent. There is obtained isopropyl 2-chloro-4-fluoro-5-[3,6-dihydro-3,4-dimethyl-5-hydroxymethyl-2,6-dioxo-1(2H)-pyrimidinyl]-benzoate, $^1$H-NMR (CDCl$_3$, 400 MHz) 7.83 ppm (d, 1H), 7.35 ppm (d, 1H), 5.24 ppm (m, 1H), 4.59 ppm (d, 1H), 4.54 ppm (d, 1H), 3.50 ppm (s, 3H), 2.44 ppm (s, 3H), 2.34 ppm (s, approx. 1H, very broad), 1.36 ppm (d, 6H).

EXAMPLE 13

1.14 g of isopropyl 2-chloro-4-fluoro-5-[5-chloromethyl-3,6-dihydro-3,4-dimethyl-2,6-dioxo-1(2H)-pyrimidinyl]-benzoate are dissolved in 10 ml of methanol and the solution is heated at 60° C. for 45 minutes. The reaction mixture is evaporated to dryness under reduced pressure and the residue is dissolved in ethyl acetate and shaken with aqueous sodium bicarbonate solution. The organic phase is dried over anhydrous sodium sulphate and evaporated to dryness under reduced pressure, and the residue is purified by chromatography on a silica gel column using diethyl ether/ethyl acetate (15:1) as the eluent. There is obtained isopropyl 2-chloro-4-fluoro-5-[3,6-dihydro-3,4-dimethyl-5-methoxymethyl-2,6-dioxo-1(2H)-pyrimidinyl]-benzoate, $^1$H-NMR (CDCl$_3$, 400 MHz) 7.82 ppm (d, 1H), 7.33 ppm (d, 1H), 5.23 ppm (m, 1H), 4.40 ppm (d, 1H), 4.33 ppm (d, 1H), 3.49 ppm (s, 3H), 3.39 ppm (s, 3H), 2.43 ppm (s, 3H), 1.35 ppm (d, 6H).

In an analogous manner, using isopropyl 2-chloro-4-fluoro-5-[5-chloromethyl-3,6-dihydro-3,4-dimethyl-2,6-dioxo-1(2H)-pyrimidinyl]-benzoate with isopropanol there is obtained isopropyl 2-chloro-4-fluoro-5-[3,6-dihydro-3,4-dimethyl-5-isopropoxymethyl-2,6-dioxo-1(2H)-pyrimidinyl]-benzoate, $^1$H-NMR (CDCl$_3$, 400 MHz) 7.82 ppm (d, 1H), 7.32 ppm (d, 1H), 5.22 ppm (m, 1H), 4.45 ppm (d, 1H), 4.34 ppm (d, 1H), 3.69 ppm (m, 1H), 3.48 ppm (s, 3H), 2.44 ppm (s, 3H), 1.35 ppm (d, 6H), 1.21 ppm (d, 6H).

EXAMPLE 14

1.14 g of isopropyl 2-chloro-4-fluoro-5-[5-chloromethyl-3,6-dihydro-3,4-dimethyl-2,6-dioxo-1(2H)-pyrimidinyl]-benzoate and 0.21 g of sodium methanethiolate in 5 ml of dimethylformamide are stirred at room temperature for 16 hours. The reaction mixture is poured into 100 ml of water and the aqueous mixture is extracted with 50 ml of ethyl acetate. The organic phase is washed with water, dried over anhydrous sodium sulphate and evaporated to dryness under reduced pressure. The residue is purified by chromatography on a silica gel column using diethyl ether/n-hexane (7:1) as the eluent. There is obtained isopropyl 2-chloro-4-fluoro-5-[3,6-dihydro-3,4-dimethyl-5-methylthiomethyl-2,6-dioxo-1(2H)-pyrimidinyl]-benzoate, $^1$H-NMR (CDCl$_3$, 400 MHz) 7.83 ppm (d, 1H), 7.33 ppm (d, 1H), 5.23 ppm (m, 1H), 3.67 ppm (d, 1H), 3.62 ppm (d, 1H), 3.50 ppm (s, 3H), 2.43 ppm (s, 3H), 2.17 ppm (s, 3H), 1.36 ppm (2xd, 6H).

EXAMPLE 15

3.40 g of isopropyl 5-[6-amino-5-cyano-2-oxo-1(2H)-pyrimidinyl]-2-chloro-4-fluorobenzoate in a solution of 100 ml isopropanol and 10 ml of 2N hydrochloric acid are stirred for 1 hour at room temperature. The reaction mixture is substantially concentrated under reduced pressure and extracted with ethyl acetate. The organic phase is washed with aqueous sodium bicarbonate solution, thereafter with water, and dried over anhydrous sodium sulphate. Then the organic phase is evaporated to dryness under reduced pressure and the residue dissolved in diethyl ether and the solution treated with charcoal and evaporated to dryness. The residue is recrystallized from diethyl ether/n-hexane. Isopropyl 2-chloro-4-fluoro-5-[5-cyano-3,6-dihydro-2,6-dioxo-1(2H)-pyrimidinyl]-benzoate, m.p. 143°–145° C., is obtained.

In an analogous manner, using isopropyl 5-[6-amino-5-cyano-4-methyl-2-oxo-1(2H)-pyrimidinyl]-2-chloro-4-fluorobenzoate there is obtained isopropyl 2-chloro-4-fluoro-5-[5-cyano-3,6-dihydro-4-methyl-2,6-dioxo-1(2H)-pyrimidiinyl]-benzoate, m.p. 189°–193° C.

EXAMPLE 16

A solution of 1.50 g of isopropyl 2-chloro-4-fluoro-5-[3,6-dihydro-4-methyl-2,6-dioxo-1(2H)-pyrimidinyl]-benzoate in 30 ml of methylene chloride at room temperature is treated with stirring with 2.0 ml of 100% nitric acid. The solution is then treated with 5 drops of concentrated sulphuric acid and stirred for 48 hours at room temperature. The reaction mixture is poured into 150 ml of ice/water, diluted with 100 ml of ethyl acetate and washed four times with 150 ml of water. The organic phase is dried over anhydrous sodium sulphate and evaporated to dryness under reduced pressure. The residue is recrystallized from diethyl ether. Isopropyl 2-chloro-4-fluoro-5-[3,6-dihydro-4-methyl-5-nitro-2,6-dioxo-1(2H)-pyrimidinyl]-benzoate, m.p. 202°–205° C., is obtained.

In an analogous manner, using isopropyl 2-chloro-4-fluoro-5-[3,6-dihydro-3,4-dimethyl-2,6-dioxo-1(2H)-pyrimidinyl]-benzoate there is obtained isopropyl 2-chloro-4-fluoro-5-[3,6-dihydro-3,4-dimethyl-5-nitro-2,6-dioxo-1(2H)-pyrimidinyl]-benzoate, m.p. 129°–131° C.

EXAMPLE 17

1.86 g of bromine in 10 ml of acetic acid are added dropwise with stirring to 2.1 g of ammonium thiocyanate in 80 ml of acetic acid at 10°–15° C. during 15 minutes. Then 1.5 g of isopropyl 2-chloro-4-fluoro-5-[3,6-dihydro-4-methyl-2,6-dioxo-1(2H)-pyrimidinyl]-benzoate in 15 ml of acetic acid are added dropwise at 10°–15° C. during 5 minutes, and the reaction mixture is stirred for a further hour at room temperature and thereafter substantially evaporated under reduced pressure. The residue is dissolved in ethyl acetate, the solid material filtered off under suction and the filtrate washed with aqueous sodium bicarbonate solution and thereafter with water. The organic phase is dried over anhydrous sodium sulphate and evaporated to dryness under reduced pressure. The residue is purified by chromatography on a silica gel column using methylene chloride/ethyl acetate (3:1) as eluent. The product is recrystallized from methylene chloride/diethyl ether. Isopropyl 2-chloro-4-fluoro-5-[3,6-dihydro-4-methyl-5-thiocyanato-2,6-dioxo-1(2H)-pyrimidinyl]-benzoate, m.p. 159°–161° C., is obtained.

In an analogous manner, using isopropyl 2-chloro-4-fluoro-5-[3,6-dihydro-3,4-dimethyl-2,6-dioxo-1(2H)-pyrimidinyl]-benzoate there is obtained isopropyl 2-chloro-4-fluoro-5-[3,6-dihydro-3,4-dimethyl-5-thiocyanato-2,6-dioxo-1(2H)-pyrimidinyl]-benzoate, $^1$H-NMR (CDCl$_3$, 400 MHz) 7.83 ppm (d 1H), 7.36 ppm (d, 1H), 5.25 ppm (m, 1H), 3.59 ppm (s, 3H), 2.80 ppm (s 3H), 1.38 ppm (d, 3H), 1.36 ppm (d, 3H).

EXAMPLE 18

3.2 g of finely powdered 2-chloro-5-(1,2,4,5,6,7-hexahydro-1-methyl-2,4-dioxo-3H-cyclopenta[d]pyrimidin-3-yl)-benzoic acid and 3.5 g of freshly distilled thionyl chloride in 60 ml of absolute benzene are heated under reflux for 5 to 6 hours while stirring until a clear solution has formed. The reaction mixture is evaporated to dryness, the acid choride is dissolved in 40 ml of absolute methylene chloride, 1.0 g of 1-methoxy-2-propanol and 0.9 g of pyridine are added and the mixture is stirred at 23° C. for 1 hour. The reaction mixture is subsequently evaporated to dryness, the residue is dissolved in ethyl acetate and the solution is washed thoroughly with water. The organic phase is dried over anhydrous sodium sulphate and evaporated to dryness. The residue is purified by chromatography on 300 g of silica gel using ethyl acetate/methylene chloride (1:3) as the eluent. There is obtained 2-methoxy-1-methylethyl 2-chloro-5-(1,2,4,5,6,7-hexahydro-1-methyl-2,4-dioxo-3H-cyclopenta[d]pyrimidin-3-yl)-benzoate, $^1$H-NMR (CDCl$_3$, 400 MHz) 7.72 ppm (d, 1H), 7.55 ppm (d, 1H), 7.27 ppm (q, 1H), 5.32 ppm (m, 1H), 3.57 ppm (q, 1H), 3.48 ppm (q, 1H), 3.39 ppm (s, 3H), 3.37 ppm (s, 3H), 2.93 ppm (m, 2H), 2.80 ppm (m, 2H), 2.15 ppm (m, 2H), 1.35 ppm (d, 3H).

In an analogous manner, using 2-chloro-5-(1,2,4,5,6,7-hexahydro-1-methyl-2,4-dioxo-3H-cyclopenta[d]pyrimidin-3-yl)-benzoic acid via the corresponding acid chloride and tert.butanol there is obtained tert.butyl 2-chloro-5-(1,2,4,5,6,7-hexahydro-1-methyl-2,4-dioxo-3H-cyclopenta[d]pyrimidin-3-yl)-benzoate, m.p. 189°–191° C., using 2-chloro-4-fluoro-5-(1,2,4,5,6,7-hexahydro-1-methyl-2,4-dioxo-3H-cyclopenta[d]pyrimidin-3-yl)-benzoic acid via the corresponding acid chloride and 1-methoxy-2-propanol there is obtained 2-methoxy-1-methylethyl 2-chloro-4-fluoro-5-(1,2,4,5,6,7-hexahydro-1-methyl-2,4-dioxo-3H-cyclopenta[d]pyrimidin-3-yl)-benzoate, $^1$H-NMR (CDCl$_3$, 400 MHz) 7.84 ppm (d, 1H), 7.34 ppm (d, 1H), 5.30 ppm (m, 1H), 3.56 ppm (q, 1H), 3.47 ppm (q, 1H), 3.40 ppm (s, 3H), 3.37 ppm (s, 3H), 2.94 ppm (m, 2H), 2.80 ppm (m, 2H), 2.16 ppm (m, 2H), 1.34 ppm (d, 3H).

using 2-chloro-4-fluoro-5-(1,2,4,5,6,7-hexahydro-1-methyl-2,4-dioxo-3H-cyclopenta[d]pyrimidin-3-yl)-benzoic acid via the corresponding acid chloride and tert.butanol there is obtained tert.butyl 2-chloro-4-fluoro-5-(1,2,4,5,6,7-hexahydro-1-methyl-2,4-dioxo-3H-cyclopenta[d]-pyrimidin-3-yl)-benzoate, $^1$H-NMR (CDCl₃, 400 MHz) 7.76 ppm (d, 1H), 7.31 ppm (d, 1H), 3.41 ppm (s, 3H), 2.94 ppm (m, 2H), 2.81 ppm (m, 2H), 2.17 ppm (m, 2H), 1.57 ppm (s, 9H).

EXAMPLE 19

A solution of 3.6 g of ethyl 2-chloro-5-[1,4,5,6,7,8-hexahydro-1-methyl-2,4-dioxo-3-(2H)-quinazolinyl]-benzoate in 70 ml of ethanol is held at 60° C. for 10 minutes with 0.6 g of sodium hydroxide in 70 ml of water and subsequently stirred for 1 hour. The solution is substantially evaporated down under reduced pressure and the residue is brought to pH 1 with 2N hydrochloric acid. The precipitate is shaken five times with 50 ml amounts of diethyl ether and the organic phases are dried over anhydrous sodium sulphate and evaporated to dryness under reduced pressure. 2-Chloro-5-[1,4,5,6,7,8-hexahydro-1-methyl-2,4-dioxo-3-(2H)-quinazolinyl]-benzoic acid is obtained.

The free acid is stirred with 0.84 g of sodium bicarbonate in 50 ml of water and the solution is evaporated to dryness under reduced pressure. The residue is evaporated to dryness three times with 50 ml amounts of absolute ethanol and triturated with a little diethyl ether, and the crystals are filtered off under suction and dried at 70° C. under reduced pressure. Sodium 2-chloro-5-[1,4,5,6,7,8-hexahydro-1-methyl-2,4-dioxo-3-(2H)-quinazolinyl]-benzoate is obtained.

1.78 g of the sodium salt are dissolved in 30 ml of absolute dimethylformamide and the solution is heated to 100° C. for 1 hour with 1.2 g of isopropyl bromide. The solvent is then removed under reduced pressure, the residue is dissolved in 100 ml of ethyl acetate, the solution is shaken with water and the organic phase is dried over anhydrous sodium sulphate. After removing the solvent the residue is crystallized from diethyl ether/n-hexane. There is obtained isopropyl 2-chloro-5-[1,4,5,6,7,8-hexahydro-1-methyl-2,4-dioxo-3-(2H)-quinazolinyl]-benzoate, m.p. 136°-138° C.

In an analogous manner, using ethyl 2-chloro-5-[1,4,5,6,7,8-hexahydro-2,4-dioxo-3-(2H)-quinazolinyl]-benzoate there is obtained isopropyl 2-chloro-5-[1,4,5,6,7,8-hexahydro-2,4-dioxo-3(2H)-quinazolinyl]-benzoate, m.p. 205°-207° C.

using ethyl 2-chloro-5-(1,2,4,5,6,7-hexahydro-1-methyl-2,4-dioxo-3H-cyclopenta[d]pyrimidin-3-yl)-benzoate via the sodium salt of the corresponding carboxylic acid and methyl iodide there is obtained methyl 2-chloro-5-(1,2,4,5,6,7-hexahydro-1-methyl-2,4-dioxo-3H-cyclopenta[d]pyrimidin-3-yl)-benzoate, m.p. 164°-166° C., using ethyl 2-chloro-5-(1,2,4,5,6,7-hexahydro-1-methyl-2,4-dioxo-3H-cyclopenta[d]pyrimidin-3-yl)-benzoate via the sodium salt of the corresponding carboxylic acid and isopropyl bromide there is obtained isopropyl 2-chloro-5-(1,2,4,5,6,7-hexahydro-1-methyl-2,4-dioxo-3H-cyclopenta[d]pyrimidin-3-yl)-benzoate, m.p 148°-150° C.

EXAMPLE 20

A solution of 26.6 g of isopropyl 2-chloro-4-fluoro-5-(1,2,4,5,6,7-hexahydro-1-methyl-2,4-dioxo-3H-cyclopenta[d]pyrimidin-3-yl)-benzoate in 1.7 l of methanol is treated with a solution of 3.08 g of sodium hydroxide in 700 ml of water. The reaction mixture is stirred at room temperature for 15 hours, during which 2.1 l of water are continuously added dropwise. Stirring is continued for a further 15 hours during which the pH value of the mixture reaches 9–10. The mixture is acidified with concentrated hydrochloric acid and concentrated under reduced pressure at approx. 20° C. to a volume of approx. 300 ml. The crystals are filtered off by suction, rinsed with a little water and dried at 40°-50° C. under reduced pressure. 2-Chloro-4-fluoro-5-(1,2,4,5,6,7-hexahydro-1-methyl-2,4-dioxo-3H-cyclopenta[d]pyrimidin-3-yl)-benzoic acid, m.p. 270°-273° C., is obtained.

18.85 g of the acid are stirred with 4.67 g of sodium bicarbonate in 300 ml of water at 50° C. for 30 minutes. The insoluble solids are filtered off under suction and the filtrate is evaporated at 40°-50° C. to dryness under reduced pressure. The residue is dissolved in 50 ml of methanol and the solution is treated with 100 ml of benzene and evaporated to dryness under reduced pressure. Subsequently evaporation to dryness under reduced pressure with a further 100 ml amount of benzene is effected. Sodium 2-chloro-4-fluoro-5-(1,2,4,5,6,7-hexahydro-1-methyl-2,4-dioxo-3H-cyclopenta[d]pyrimidin-3-yl)-benzoate is obtained.

1.9 g of the sodium salt are dissolved in 15 ml of absolute dimethylformamide and stirred for 2 hours at 70° C. with 0.6 g of 3-bromo-1-propene. The solvent is distilled off under reduced pressure and the residue is dissolved in ethyl acetate/diethyl ether and shaken with water. The organic phase is dried over anhydrous sodium sulphate and evaporated to dryness under reduced pressure. 2-Propenyl 2-chloro-4-fluoro-5-(1,2,4,5,6,7-hexahydro-1-methyl-2,4-dioxo-3H-cyclopenta[d]pyrimidin-3-yl)-benzoate is obtained, ¹H-NMR (CDCl₃, 400 MHz) 7.90 ppm (d, 1H), 7.35 ppm (d, 1H), 6.05–5.94 ppm (m, 1H), 5.40 ppm (m, 1H), 5.29 (m, 1H), 4.79 ppm (m, 2H), 3.41 ppm (s, 3H), 2.94 ppm (m, 2H), 2.81 ppm (m, 2H), 2.16 ppm (m, 2H).

In an analogous manner, using sodium 2-chloro-4-fluoro-5-(1,2,4,5,6,7-hexahydro-1-methyl-2,4-dioxo-3H-cyclopenta[d]pyrimidin-3-yl)-benzoate and chlorodimethyl ether there is obtained methoxymethyl 2-chloro-4-fluoro-5-(1,2,4,5,6,7-hexahydro-1-methyl-2,4-dioxo-3H-cyclopenta[d]pyrimidin-3-yl)-benzoate, ¹H-NMR (CDCl₃, 400 MHz) 7.93 ppm (d, 1H), 7.36 ppm (d, 1H), 5.45 ppm (s, 2H), 3.54 ppm (s, 3H), 3.41 ppm (s, 3H), 2.95 ppm (m, 2H), 2.81 ppm (m, 2H), 2.17 ppm (m, 2H), using sodium 2-chloro-4-fluoro-5-(1,2,4,5,6,7-hexahydro-1-methyl-2,4-dioxo-3H-cyclopenta[d]pyrimidin-3-yl)-benzoate and 3-bromo-1-propyne there is obtained 2-propynyl 2-chloro-4-fluoro-5-(1,2,4,5,6,7-hexahydro-1-methyl-2,4-dioxo-3H-cyclopenta[d]pyrimidin-3-yl)-benzoate, m.p. 193°-195° C.

using sodium 2-chloro-4-fluoro-5-(1,2,4,5,6,7-hexahydro-1-methyl-2,4-dioxo-3H-cyclopenta[d]pyrimidin-3-yl)-benzoate and methyl iodide there is obtained methyl 2-chloro-4-fluoro-5-(1,2,4,5,6,7-hexahydro-1-methyl-2,4-dioxo-3H-cyclopenta[d]pyrimidin-3-yl)-benzoate, m.p. 138°-141° C.

II. Production of the compounds of formula II:

EXAMPLE 21

48.4 g of ethyl 2-chloro-5-ureido-benzoate and 31.2 g of ethyl cyclopentanone-2-carboxylate are heated under reflux for 6 hours in 500 ml of benzene and 2 g of toluene-4-sulphonic acid monohydrate. The water formed is removed by means of a water separator. The reaction mixture is subsequently evaporated to dryness, the residue is dissolved in 700 ml of diethyl ether and the solution is filtered. The filtrate is evaporated to dryness and the residue is purified by chromatography on 1.5 g of silica gel using diethyl ether/n-hexane (1:2) as the eluent. There is obtained ethyl 2-chloro-5-{3-[2-(ethoxycarbonyl)-1-cyclopenten-1-yl]ureido}-benzoate as colourless crystals. The product is recrystallized from diethyl ether/n-hexane, m.p. 110°–112° C.

In in analogous manner, using ethyl 2-chloro-5-ureidobenzoate and ethyl cyclohexanone-2-carboxylate there is obtained ethyl 2-chloro-5-{3-[2-(ethoxycarbonyl)-1-cyclohexen-1-yl]ureido}-benzoate, m.p. 119°–122° C., using isopropyl 2-chloro-4-fluoro-5-ureidobenzoate and ethyl cyclopentanone-2-carboxylate there is obtained isopropyl 2-chloro-4-fluoro-5-{3-[2-(ethoxycarbonyl)-1-cyclopenten-1-yl]ureido}-benzoate, m.p. 146°–149° C., using isopropyl 2-chloro-4-fluoro-5-ureidobenzoate and ethyl cyclohexanone-2-carboxylate there is obtained isopropyl 2-chloro-4-fluoro-5-{3-[2-(ethoxycarbonyl)-1-cyclohexen-1-yl]ureido}-benzoate, m.p. 129°–130° C., using ethyl 2-nitro-5-ureidobenzoate and ethyl cyclopentanone-2-carboxylate there is obtained ethyl 5-{3-[2-(ethoxycarbonyl)-1-cyclopenten-1-yl]ureido}-2-nitrobenzoate, m.p. 152°–155° C., using isopropyl 2-chloro-4-fluoro-5-ureidobenzoate and methyl 3-oxotetrahydrothiophene-2-carboxylate there is obtained isopropyl 2-chloro-4-fluoro-5-{3-[2-(methoxycarbonyl)-4,5-dihydro-thien-3-yl]ureido}-benzoate, m.p. 161°–163° C., using isopropyl 2-chloro-4-fluoro-5-ureidobenzoate and methyl 3-oxotetrahydrothiophene-4-carboxylate there is obtained isopropyl 2-chloro-4-fluoro-5-{3-[4-(methoxycarbonyl)-2,5-dihydro-thien-3-yl]ureido}-benzoate, using ethyl 2-chloro-5-ureidobenzoate and methyl 3-oxotetrahydrothiophene-4-carboxylate there is obtained ethyl 2-chloro-5-{3-[4-(methoxycarbonyl)-2,5-dihydro-thien-3-yl]ureido}-benzoate, using isopropyl 2-chloro-4-fluoro-5-ureidobenzoate and ethyl 3-oxo-caproate there is obtained isopropyl 2-chloro-4-fluoro-5-{3-[2-(ethoxycarbonyl)-1-propylvinyl]ureido}-benzoate, using isopropyl 2-chloro-4-fluoro-5-ureidobenzoate and ethyl 3-oxo-n-valerate and finely powdered Amberlyst®-15 (an organic polymeric resin featuring free sulphone groups) as catalyst there is obtained isopropyl 2-chloro-4-fluoro-5-{3-[2-(ethoxycarbonyl)-1-ethylvinyl]ureido}-benzoate, m.p. 123°–126° C.

using isopropyl 2,4-difluoro-5-ureidobenzoate and ethyl cyclopentanone-2-carboxylate in toluene there is obtained isopropyl 2,4-difluoro-5-{3-[2-(ethoxycarbonyl)-1-cyclopenten-1-yl]ureido}-benzoate, m.p. 149°–151° C.

using isopropyl 2,4-dichloro-5-ureidobenzoate and ethyl cyclopentanone-2-carboxylate and finely powdered Amberlyst®-15 as catalyst there is obtained isopropyl 2,4-dichloro-5-{3-[2-(ethoxycarbonyl)-1-cyclopenten-1-yl]ureido}-benzoate, m.p. 140°–142° C., using isopropyl 2-bromo-4-chloro-5-ureidobenzoate and ethyl cyclopentanone-2-carboxylate in toluene there is obtained isopropyl 2-bromo-4-chloro-5-{3-[2-(ethoxycarbonyl)-1-cyclopenten-1-yl]ureido}-benzoate, m.p. 131°–132° C.

using isopropyl 2,4-dibromo-5-ureidobenzoate and ethyl cyclopentanone-2-carboxylate in toluene there is obtained isopropyl 2,4-dibromo-5-{3-[2-(ethoxycarbonyl)-1-cyclopenten-1-yl]ureido}-benzoate, m.p. 157°–158° C., using isopropyl 2-bromo-4-fluoro-5-ureidobenzoate and ethyl cyclopentanone-2-carboxylate in toluene there is obtained isopropyl 2-bromo-4-fluoro-5-{3-[2-(ethoxycarbonyl)-1-cyclopenten-1-yl]ureido}-benzoate, m.p. 150°–154° C., using isopropyl 4-bromo-2-fluoro-5-ureidobenzoate and ethyl cyclopentanon-2-carboxylate in toluene there is obtained isopropyl 4-bromo-2-fluoro-5-{3-[2-(ethoxycarbonyl)-1-cyclopenten-1-yl]ureido}-benzoate, m.p. 166°–168° C.

EXAMPLE 22

4.7 g of ethyl 3-amino-2-methylcrotonate, dissolved in 15 ml of absolute diethyl ether, are treated at 23° C. while stirring with a solution of 6.7 g of ethyl 2-chloro-5-isocyanatobenzoate and stirred for 2 hours. The reaction mixture is evaporated to dryness under reduced pressure and the residue is purified by chromatography on 400 g of silica gel using diethyl ether/n-hexane (1:1) as the eluent. There is obtained ethyl 2-chloro-5-{3-[2-(ethoxycarbonyl)-1-methylpropenyl]ureido}-benzoate, m.p. 88°–91° C.

In an analogous manner, using isopropyl 2-chloro-4-fluoro-5-isocyanatobenzoate and ethyl 3-amino-2-methylcrotonate there is obtained isopropyl 2-chloro-4-fluoro-5-{3-[2-(ethoxycarbonyl)-1-methylpropenyl]ureido}-benzoate, m.p. 145°–147° C., using ethyl 2-chloro-5-isocyanatobenzoate and ethyl 3-aminocrotonate there is obtained ethyl 2-chloro-5-{3-[2-(ethoxycarbonyl)-1-methylvinyl]ureido}-benzoate, using isopropyl 2-chloro-4-fluoro-5-isocyanatobenzoate and ethyl 3-aminocrotonate there is obtained isopropyl 2-chloro-4-fluoro-5-{3-[2-(ethoxycarbonyl)-1-methylvinyl]ureido}benzoate, m.p. 147°–150° C., using isopropyl 2-chloro-4-fluoro-5-isocyanatobenzoate and ethyl 3-amino-2-fluorocrotonate there is obtained isopropyl 2-chloro-4-fluoro-5-{3-[2-(ethoxycarbonyl)-2-fluoro-1-methylvinyl]ureido}-benzoate, m.p. 150°–152° C., using isopropyl 2-chloro-4-fluoro-5-isocyanatobenzoate and ethyl 3-amino-2-ethylcrotonate in dimethylformamide there is obtained isopropyl 2-chloro-4-fluoro-5-{3-[2-(ethoxycarbonyl)-1-methyl-1-butenyl]ureido}-benzoate, m.p. 112°–115° C., using isopropyl 2-chloro-4-fluoro-5-isocyanatobenzoate and ethyl 3-amino-2-methyl-2-pentanoate there is obtained isopropyl 2-chloro-4-fluoro-5-{3-[2-(ethoxycarbonyl)-1-ethyl-1-propenyl]ureido}-benzoate, m.p. 132°–133° C., using isopropyl 2-chloro-4-fluoro-5-isocyanatobenzoate and ethyl 2-amino-4,5-dihydrofuran-3-carboxylate there is obtained isopropyl 2-chloro-4-fluoro-5-[3-[3-(ethoxycarbonyl)-4,5-dihydro-furan-2-yl]ureido}-benzoate.

EXAMPLE 23

6.0 g of ethyl 2-chloro-5-ureidobenzoate and 6.4 g of ethyl 3-ethoxyacrylate are heated at reflux temperature in 100 ml of 1,2-dimethoxyethane and subsequently heated at this temperature with 12 ml of 2N hydrochloric acid for 5 minutes. The reaction mixture is evaporated to dryness under reduced pressure and the residue is purified by chromatography on 300 g of silica gel using ethyl acetate/n-hexane (1:3) as the eluent. There is obtained ethyl 2-chloro-5-{3-[2-(ethoxycarbonyl)vinyl]ureido}-benzoate, m.p. 116°–117° C.

EXAMPLE 24

27.4 g of isopropyl 2-chloro-4-fluoro-5-ureidobenzoate and 13.0 g of methyl 3-methoxy-2-methyl-acrylate are heated under reflux for 2 hours in 250 ml of benzene with 1.9 g of toluene-4-sulphonic acid monohydrate. The reaction mixture is evaporated to dryness under reduced pressure and the residue is stirred with 400 ml of diethyl ether. The insoluble material is filtered off under suction and the filtrate is evaporated to dryness under reduced pressure. The residue is purified by chromatography on 1 kg of silica gel using ethyl acetate/n-hexane (1:3) as the eluent. There is obtained isopropyl 2-chloro-4-fluoro-5-{3-[2-(methoxycarbonyl)propenyl-]ureido}-benzoate, m.p. 189°–190° C.

III. Manufacture of the compounds of formula VI:

EXAMPLE 25

To 0.71 g of a 55% sodium hydride dispersion in 25 ml of dimethylformamide are introduced 1.52 g of 3-amino-2-cyanoacrylonitril, and the mixture is stirred for 30 minutes at 30° C. After completion of the hydrogen evolution the mixture is treated with 4.20 g of isopropyl 2-chloro-4-fluoro-5-isocyanatobenzoate, during which the temperature rises to 30° C. The reaction mixture is then stirred for a further 2 hours at room temperature and poured into water, and the aqueous mixture is acidified with acetic acid and extracted twice with 100 ml of ethyl acetate. The organic phase is washed with water, dried over anhydrous sodium sulphate and evaporated to dryness under reduced pressure. The residue is dissolved in 50 ml of methylene chloride and crystallization induced by addition of diethyl ether and cooling to 0° C. Isopropyl 5-[6-amino-5-cyano-2-oxo-1(2H)-pyrimidinyl]-2-chloro-4-fluorobenzoate, m.p. 212°–213° C., is obtained.

In an analogous manner, using 3-amino-2-cyanocrotononitrile and isopropyl 2-chloro-4-fluoro-5-isocyanatobenzoate there is obtained isopropyl 5-[6-amino-5-cyano-4-methyl-2-oxo-1(2H)-pyrimidinyl]-2-chloro-4-fluorobenzoate, m.p. 255°–257° C.

IV. Formulation Examples:

EXAMPLE 26

For the manufacture of a 50% spray powder the ingredients listed hereinafter are mixed with one another.

| Compound of formula I' or II | 50 g |
| --- | --- |
| Silicic acid, hydrated | 5 g |
| Sodium lauryl sulphate | 1 g |
| Sodium lignosulphonate | 2 g |
| Kaolin | 42 g |
| | 100 g |

This mixture is finely ground in a suitable mill.
What is claimed is:
1. Compounds of the formula

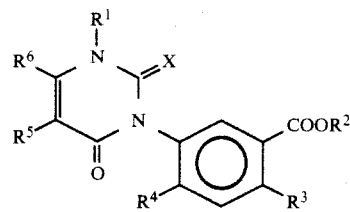

wherein
$R^1$ signifies hydrogen, $C_{1-4}$-alkyl, $C_{2-4}$-alkenyl, $C_{2-4}$-alkynyl, $C_{2-6}$-alkoxyalkyl, formyl, $C_{2-6}$-alkanoyl or $C_{2-6}$-alkoxycarbonyl,
$R^2$ signifies hydrogen, $C_{1-6}$-alkyl, $C_{2-4}$-alkenyl, $C_{2-4}$-alkynyl or $C_{2-6}$-alkoxyalkyl,
$R^3$ signifies halogen or nitro,
$R^4$ signifies hydrogen or halogen,
$R^5$ signifies hydrogen, halogen, $C_{1-4}$-alkyl, chloromethyl, bromomethyl, hydroxymethyl, ($C_{1-5}$-alkoxy)methyl, ($C_{1-5}$-alkylthio)methyl, cyano, nitro or thiocyanato,
$R^6$ signifies hydrogen, $C_{1-4}$-alkyl or $C_{1-4}$-fluoroalkyl, or
$R^5$ and $R^6$ together signify tri- or tetramethylene in which one methylene can be replaced by oxygen or sulphur and which is optionally substituted with $C_{1-3}$-alkyl, and
X signifies oxygen or sulphur, with the provisos that (i) $R^6$ is $C_{1-4}$-alkyl or $C_{1-4}$-fluoroalkyl when $R^5$ is fluorine and (ii) $R^6$ is hydrogen or $C_{1-4}$-alkyl and X is oxygen when $R^5$ is cyano,
as well as the alkali metal, alkaline earth metal, ammonium and organic base salts of those compounds of formula I in which $R^1$ and/or $R^2$ signifies hydrogen.

2. Compounds of the formula

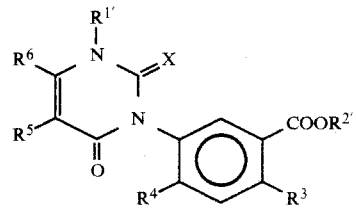

wherein
$R^{1'}$ signifies $C_{1-4}$-alkyl, $C_{2-4}$-alkenyl, $C_{2-4}$-alkynyl, $C_{2-6}$-alkoxyalkyl, formyl, $C_{2-6}$-alkanoyl or $C_{2-6}$-alkoxycarbohyl,
$R^{2'}$ signifies $C_{1-6}$-alkyl, $C_{2-4}$-alkenyl, $C_{2-4}$-alkynyl or $C_{2-6}$-alkoxyalkyl,
$R^3$ signifies halogen or nitro,
$R^4$ signifies hydrogen or halogen,
$R^5$ signifies hydrogen, halogen, $C_{1-4}$-alkyl, chloromethyl, bromomethyl, hydroxymethyl, ($C_{1-5}$-alkoxy)methyl, ($C_{1-5}$-alkylthio)methyl, cyano, nitro or thiocyanato,
$R^6$ signifies hydrogen, $C_{1-4}$-alkyl or $C_{1-4}$-fluoroalkyl, or
$R^5$ and $R^6$ together signify tri- or tetramethylene in which one methylene can be replaced by oxygen or sulphur and which is optionally substituted with $C_{1-2}$-alkyl, and
X signifies oxygen or sulphur, with the provisos that (i) $R^6$ is $C_{1-4}$-alkyl or $C_{1-4}$-fluoroalkyl when $R^5$ is fluorine and (ii) $R^6$ is hydrogen or $C_{1-4}$-alkyl and X is oxygen when $R^5$ is cyano.

3. Compounds according to claim 2, wherein $R^{1'}$ signifies methyl.

4. Compounds according to claim 2, wherein $R^{2'}$ signifies $C_{1-6}$-alkyl or $C_{2-6}$-alkoxyalkyl.

5. Compounds according to claim 2, wherein $R^3$ signifies chlorine or bromine.

6. Compounds according to claim 2, wherein $R^4$ signifies fluorine.

7. Compounds according to claim 2, wherein $R^5$ signifies hydrogen, chlorine, bromine, methyl or ethyl.

8. Compounds according to claim 2, wherein $R^5$ signifies fluorine.

9. Compounds according to claim 2, wherein $R^6$ signifies methyl, ethyl or trifluoromethyl.

10. Compounds according to claim 2, wherein $R^5$ and $R^6$ together signify tri- or tetramethylene.

11. A compound according to claim 2, selected from:
Isopropyl 2-chloro-4-fluoro-5-(1,2,4,5,6,7-hexahydro-1-methyl-2,4-dioxo-3H-cyclopenta[d]pyrimidin-3-yl)-benzoate,
isopropyl 2-chloro-4-fluoro-5-[1,4,5,6,7,8-hexahydro-1-methyl-2,4-dioxo-3(2H)-quinazolinyl]-benzoate,
isopropyl 2-chloro-4-fluoro-5-[3,6-dihydro-3,4-dimethyl-2,6-dioxo-1-(2H)-pyrimidinyl]-benzoate,
isopropyl 2-chloro-4-fluoro-5-[5-bromo-3,6-dihydro-3,4-dimethyl-2,6-dioxo-1-(2H)-pyrimidinyl]-benzoate,
isopropyl 2-chloro-4-fluoro-5-[3,6-dihydro-3,4-dimethyl-5-iodo-2,6-dioxo-1(2H)-pyrimidinyl]-benzoate,
isopropyl 2-chloro-4-fluoro-5-[3,6-dihydro-3,4-dimethyl-5-hydroxymethyl-2,6-dioxo-1(2H)-pyrimidinyl]-benzoate,
isopropyl 2-chloro-4-fluoro-5-[3,6-dihydro-4-ethyl3-methyl-2,6-dioxo-1(2H)-pyrimidinyl]-benzoate,
isopropyl 2-chloro-4-fluoro-5-[3,6-dihydro-3-methyl-4-trifluoromethyl-2,6-dioxo-1(2H)-pyrimidinyl]-benzoate,
isopropyl 2-bromo-4-fluoro-5-(1,2,4,5,6,7-hexahydro-1-methyl-2,4-dioxo-3H-cyclopenta[d]pyrimidin-3-yl)-benzoate,
isopropyl 2-chloro-4-fluoro-5-[3,6-dihydro-3,4-dimethyl-5-nitro-2,6-dioxo-1(2H)-pyrimidinyl]benzoate,
2-methoxy-1-methylethyl 2-chloro-4-fluoro-5-(1,2,4,5,6,7-hexahydro-1-methyl-2,4-dioxo-3H-cyclopenta[d]pyrimidin-3-yl)-benzoate and
tert.-butyl 2-chloro-4-fluoro-5-(1,2,4,5,6,7-hexahydro-1-methyl-2,4-dioxo-3H-cyclopenta[d]pyrimidin-3-yl)-benzoate.

12. A compound according to claim 2, selected from:
Isopropyl 2-chloro-4-fluoro-5-[3,6-dihydro-3,4-dimethyl-5-fluoro-2,6-dioxo-1(2H)-pyrimidinyl]-benzoate,
isopropyl 2-chloro-4-fluoro-5-[3,6-dihydro-3-methyl-4-propyl-2,6-dioxo-1(2H)-pyrimidinyl]-benzoate and
isopropyl 2-chloro-4-fluoro-5-[3,6-dihydro-5-fluoro-3-methyl-4-trifluoromethyl-2,6-dioxo-1(2H)-pyrimidinyl]-benzoate.

13. A compound according to claim 1, selected from:
Ethyl 2-chloro-5-(1,2,4,5,6,7-hexahydro-2,4-dioxo-3H-cyclopenta[d]pyrimidin-3-yl)-benzoate,
isopropyl 2-chloro-4-fluoro-5-(1,2,4,5,6,7-hexahydro-2,4-dioxo-3H-cyclopenta[d]pyrimidin-3-yl)-benzoate,
isopropyl 2-chloro-4-fluoro-5-[1,4,5,6,7,8-hexahydro-2,4-dioxo-3(2H)-quinazolinyl]-benzoate,
isopropyl 2-chloro-4-fluoro-5-[3,6-dihydro-5-methyl-2,6-dioxo-1(2H)-pyrimidinyl]-benzoate,
isopropyl 2-bromo-4-fluoro-5-(1,2,4,5,6,7-hexahydro-2,4-dioxo-3H-cyclopenta[d]pyrimidin-3-yl)-benzoate,
isopropyl 2-chloro-4-fluoro-5-{1,2,5,7-tetrahydro-2,4-dioxo-thieno[3,4-d]pyrimidin-3(4H)-yl}-benzoate,
Isopropyl 2-chloro-5-[1,4,5,6,7,8-hexahydro-2,4-dioxo-3(2H)-quinazolinyl]-benzoate.

14. A compound according to claim 2, selected from:
isopropyl 2-chloro-4-fluoro-5-[3,6-dihydro-4-methyl-2,6-dioxo-1(2H)-pyrimidinyl]-benzoate,
isopropyl 2-chloro-4-fluoro-5-[3,6-dihydro-4-ethyl-5-methyl-2,6-dioxo-1(2H)-pyrimidinyl]-benzoate,
ethyl 2-chloro-5-(1,2,4,5,6,7-hexahydro-1-methyl-2,4-dioxo-3H-cyclopenta[d]pyrimidin-3-yl)-benzoate,
ethyl 2-chloro-5-[1,4,5,6,7,8-hexahydro-1-methyl-2,4-dioxo-3(2H)-quinazolinyl]-benzoate,
ethyl 2-chloro-4-fluoro-5-[3,6-dihydro-4-ethyl-2,6-dioxo-1(2H)-pyrimidinyl]-benzoate,
ethyl 2-chloro-5-[3,6-dihydro-3,4-dimethyl-2,6-dioxo-1(2H)-pyrimidinyl]-benzoate,
ethyl 2-chloro-5-[3,6-dihydro-3,4,5-trimethyl-2,6-dioxo-1(2H)-pyrimidinyl]-benzoate,
isopropyl 2-chloro-4-fluoro-5-[3,6-dihydro-3,4,5-trimethyl-2,6-dioxo-1(2H)-pyrimidinyl]-benzoate,
isopropyl 2-chloro-4-fluoro-5-{1,2,5-tetrahydro-1-methyl-2,4-dioxo-thieno[3,4-d]pyrimidin-3(4H)-yl}-benzoate,
isopropyl 2-chloro-4-fluoro-5-[3,6-dihydro-3,5-dimethyl-4-ethyl-2,6-dioxo-1(2H)-pyrimidinyl]-benzoate,
isopropyl 2-chloro-4-fluoro-5-[5-cyano-3,6-dihydro-3,4-dimethyl-2,6-dioxo-1(2H)-pyrimidinyl]-benzoate,
isopropyl 2,4-dichloro-5-(1,2,4,5,6,7-hexahydro-1-methyl-2,4-dioxo-3H-cyclopenta[d]pyrimidin-3-yl)-benzoate,
isopropyl 2-bromo-4-chloro-5-(1,2,4,5,6,7-hexahydro-1-methyl-2,4-dioxo-3H-cyclopenta[d]pyrimidin-3-yl)-benzoate,
isopropyl 2-chloro-4-fluoro-5-(1,2,4,5,6,7-hexahydro-1-acetyl-2,4-dioxo-3H-cyclopenta[d]pyrimidin-3yl)-benzoate,
isopropyl 2-chloro-4-fluoro-5-{1,2,4,5,6,7-hexahydro-1-methoxycarbonyl-2,4-dioxo-3H-cyclopenta[d]pyrimidin-3-yl}-benzoate,
isopropyl 2-chloro-4-fluoro-5-[5-chloro-3,6-dihydro-3,4-dimethyl-2,6-dioxo-1(2H)-pyrimidinyl]-benzoate,
isopropyl 2-chloro-4-fluoro-5-[5-bromo-3,6-dihydro-4-methyl-2,6-dioxo-1(2H)-pyrimidinyl]-benzoate,
tert.butyl 2-chloro-5-(1,2,4,5,6,7-hexahydro-1-methyl-2,4-dioxo-3H-cyclopenta[d]pyrimidin-3-yl)-benzoate,
isopropyl 2-chloro-5-[1,4,5,6,7,8-hexahydro-1-methyl-2,4-dioxo-3(2H)-quinazolinyl]-benzoate,
2-propenyl 2-chloro-4-fluoro-5-(1,2,4,5,6,7-hexahydro-1-methyl-2,4-dioxo-3H-cyclopenta[d]pyrimidin-3-yl)-benzoate,
2-propynyl 2-chloro-4-fluoro-5-(1,2,4,5,6,7-hexahydro-1-methyl-2,4-dioxo-3H-cyclopenta[d]pyrimidin-3-yl)-benzoate and
methyl 2-chloro-4-fluoro-5-(1,2,4,5,6,7-hexahydro-1-methyl-2,4-dioxo-3H-cyclopenta[d]pyrimidin-3-yl)-benzoate.

15. A compound according to claim 2, selected from:
Isopropyl 2-chloro-4-fluoro-5-[3,6-dihydro-5-fluoro-4-methyl-2,6-dioxo-1(2H)-pyrimidinyl]-benzoate,
isopropyl 2-chloro-4-fluoro-5-[3,6-dihydro-5-fluoro-4-fluoromethyl-2,6-dioxo-1(2H)-pyrimidinyl]-benzoate,
isopropyl 2-chloro-4-fluoro-5-[3,6-dihydro-5-fluoro-4-fluoromethyl-3-methyl-2,6-dioxo-1(2H)-pyrimidinyl]-benzoate, isopropyl 2-chloro-4-fluoro-5-[3,6-dihydro-4-propyl-2,6-dioxo-1(2H)-pyrimidinyl]-benzoate, isopropyl 2-chloro-4-fluoro-5-[5-chloro-3,6-dihydro-4-methyl-2,6-dioxo-1(2H)-pyrimidinyl]-benzoate and isopropyl 2-chloro-4-fluoro-5-[3,6-dihydro-3,4-dimethyl-5-methoxymethyl-2,6-dioxo-1(2H)-pyrimidinyl]-benzoate.

16. A weed control composition, characterized in that it contains an effective amount of at least one compound of the formula

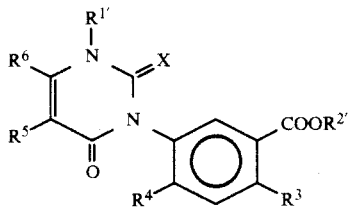       I' wherein

R$^{1'}$ signifies hydrogen, C$_{1-4}$-alkyl, C$_{2-4}$-alkenyl, C$_{2-4}$-alkynyl, C$_{2-6}$-alkoxyalkyl, formyl, C$_{2-6}$-alkanoyl or C$_{2-6}$-alkoxycarbonyl, R$^{2'}$ signifies hydrogen, C$_{1-6}$-alkyl, C$_{2-4}$-alkenyl, C$_{2-4}$-alkynyl or C$_{2-6}$-alkoxyalkyl, R$^3$ signifies halogen or nitro, R$^4$ signifies hydrogen or halogen, R$^5$ signifies hydrogen, halogen, C$_{1-4}$alkyl, chloromethyl, bromomethyl, hydroxymethyl, (C$_{1-5}$alkoxy)methyl, (C$_{1-5}$-alkylthio)methyl, cyano, nitro or thiocyanato, R$^6$ signifies hydrogen, C$_{1-4}$-alkyl or C$_{1-4}$-fluoroalkyl, or R$^5$ and R$^6$ together signify tri- or tetramethylene in whcih one methylene can be replaced by oxygen or sulphur and which is optionally substituted with C$_{1-3}$-alkyl, and X signifies oxygen or sulphur, with the provisos that (i) R$^6$ is C$_{1-4}$-alkyl or C$_{1-4}$-fluoroalkyl when R$^5$ is fluorine and (ii) R$^6$ is hydrogen or C$_{1-4}$-alkyl and X is oxygen when R$^5$ is cyano as well as formulation adjuvants.

17. A weed control composition according to claim 16, characterized in that it contains an effective amount of at least one compound selected from the group:

Isopropyl 2-chloro-4-fluoro-5-(1,2,4,5,6,7-hexahydro-1-methyl-2,4-dioxo-3H-cyclopenta[d]pyrimidin-3-yl)-benzoate, isopropyl 2-chloro-4-fluoro-5-[1,4,5,6,7,8-hexahydro-1-methyl-2,4-dioxo-3(2H)-quinazolinyl]-benzoate, isopropyl 2-chloro-4-fluoro-5-[3,6-dihydro-3,4-dimethyl-2,6-dioxo-1(2H)-pyrimidinyl]-benzoate, isopropyl 2-chloro-4-fluoro-5-[5-bromo-3,6-dihydro-3,4-dimethyl-2,6-dioxo-1(2H)-pyrimidinyl]-benzoate, isopropyl 2-chloro-4-fluoro-5-[3,6-dihydro-3,4-dimethyl-5-iodo-2,6-dioxo-1(2H)-pyrimidinyl]-benzoate, isopropyl 2-chloro-4-fluoro-5-[3,6-dihydro-3,4-dimethyl-5-hydroxymethyl-2,6-dioxo-1(2H)-pyrimidinyl]-benzoate, isopropyl 2-chloro-4-fluoro-5-[3,6-dihydro-4-ethyl-3-methyl-2,6-dioxo-1(2H)-pyrimidinyl]-benzoate, isopropyl 2-chloro-4-fluoro-5-[3,6-dihydro-3-methyl-4-trifluoromethyl-2,6-dioxo-1(2H)-pyrimidinyl]-benzoate, isopropyl 2-bromo-4-fluoro-5-(1,2,4,5,6,7-hexahydro-1-methyl-2,4-dioxo-3H-cyclopenta[d]pyrimidin-3-yl)-benzoate, isopropyl 2-chloro-4-fluoro-5-[3,6-dihydro-3,4-dimethyl-5-nitro-2,6-dioxo-1(2H)-pyrimidinyl]benzoate, 2-methoxy-1-methylethyl 2-chloro-4-fluoro-5-(1,2,4,5,6,7-hexahydro-1-methyl-2,4-dioxo-3H-cyclopenta[d]pyrimidin-3-yl)-benzoate and tert.butyl 2-chloro-4-fluoro-5-(1,2,4,5,6,7-hexahydro-1-methyl-2,4-dioxo-3H-cyclopenta[d]pyrimidin-3-yl)-benzoate as well as formulation adjuvants.

18. A weed control composition according to claim 16, characterized in that it contains an effective amount of at least one compound selected from the group:

Isopropyl 2-chloro-4-fluoro-5-[3,6-dihydro-3,4-dimethyl-5-fluoro-2,6-dioxo-1(2H)-pyrimidinyl]-benzoate, isopropyl 2-chloro-4-fluoro-5-[3,6-dihydro-3-methyl-4-propyl-2,6-dioxo-1(2H)-pyrimidinyl]-benzoate and isopropyl 2-chloro-4-fluoro-5-[3,6-dihydro-5-fluoro-3-methyl-4-trifluoromethyl-2,6-dioxo-1(2H)-pyrimidinyl]-benzoate as well as formulation adjuvants.

19. A method for the control of weeds, characterized by treating the locus to be protected against weeds and/or the weeds with an effective amount of a composition in accordance with claim 16.

20. A method for the control of weeds, characterized by treating the locus to be protected against weeds and/or the weeds with an effective amount of a composition in accordance with claim 17.

21. A method for the control of weeds, characterized by treating the locus to be protected against weeds and/or the weeds with an effective amount of a composition in accordance with claim 18.

* * * * *